(12) United States Patent
Hartwig et al.

(10) Patent No.: US 12,390,457 B2
(45) Date of Patent: Aug. 19, 2025

(54) STABLE SOLUTIONS OF IMMUNOMODULATORY IMIDE COMPOUNDS FOR PARENTERAL USE

(71) Applicant: Starton Therapeutics, Inc., Paramus, NJ (US)

(72) Inventors: Rod L. Hartwig, Sloatsburg, NY (US); Arturo Serrano-Batista, Sloatsburg, NY (US); James Oliver, Raleigh, NC (US)

(73) Assignee: Starton Therapeutics, Inc., Paramus, NJ (US)

( * ) Notice: Subject to any disclaimer, the term of this patent is extended or adjusted under 35 U.S.C. 154(b) by 82 days.

(21) Appl. No.: 17/570,463

(22) Filed: Jan. 7, 2022

(65) Prior Publication Data

US 2022/0218687 A1    Jul. 14, 2022

Related U.S. Application Data

(60) Provisional application No. 63/135,347, filed on Jan. 8, 2021.

(51) Int. Cl.
| | |
|---|---|
| *A61K 31/454* | (2006.01) |
| *A61K 31/5377* | (2006.01) |
| *A61K 47/02* | (2006.01) |
| *A61K 47/12* | (2006.01) |
| *A61K 47/32* | (2006.01) |

(52) U.S. Cl.
CPC ........ *A61K 31/454* (2013.01); *A61K 31/5377* (2013.01); *A61K 47/02* (2013.01); *A61K 47/12* (2013.01); *A61K 47/32* (2013.01)

(58) Field of Classification Search
CPC .. A61K 31/454; A61K 31/5377; A61K 47/02; A61K 47/12; A61K 47/32; A61K 9/0019; A61K 47/22; A61K 9/08; A61P 29/00; A61P 35/00
USPC ...................................................... 514/235
See application file for complete search history.

(56) References Cited

U.S. PATENT DOCUMENTS

| | | | |
|---|---|---|---|
| 6,124,322 A | 9/2000 | Bjoerkman et al. | |
| 9,724,329 B2 | 8/2017 | Hsu et al. | |
| 10,159,714 B2* | 12/2018 | Leung | A61K 38/26 |
| 10,328,028 B2* | 6/2019 | Vivancos Martinez et al. | A61K 9/1635 |
| 11,007,152 B2 | 5/2021 | Vivancos Martinez et al. | |
| 11,197,852 B2* | 12/2021 | Borovinskaya | A61K 31/5377 |
| 2007/0208057 A1 | 9/2007 | Zeldis | |
| 2010/0278779 A1 | 11/2010 | Zeldis | |
| 2013/0302377 A1 | 11/2013 | Hsu et al. | |
| 2013/0338103 A1* | 12/2013 | Ryan et al. | A61K 47/4823 514/58 |
| 2017/0038387 A1 | 2/2017 | Gandhi et al. | |
| 2018/0256501 A1 | 9/2018 | Vivancos Martinez et al. | |
| 2019/0060221 A1 | 2/2019 | Joharapurkar et al. | |
| 2019/0240157 A1 | 8/2019 | Vivancos Martinez et al. | |
| 2019/0300620 A1* | 10/2019 | Nasoff et al. | C07K 16/2896 |
| 2020/0330445 A1* | 10/2020 | Borovinskaya | A61P 35/00 |

FOREIGN PATENT DOCUMENTS

| | | | | |
|---|---|---|---|---|
| CN | 101336890 A | * | 1/2009 | |
| WO | WO 2005/046593 A2 | | 5/2005 | |
| WO | WO 2011/160170 A1 | | 12/2011 | |
| WO | WO 2017/109041 A1 | | 6/2017 | |
| WO | WO-2017216738 A1 | * | 12/2017 | ......... A61K 31/4035 |
| WO | WO 2018/138737 A1 | | 8/2018 | |

OTHER PUBLICATIONS

Usach, I., Martinez, R., Festini, T. et al. Subcutaneous Injection of Drugs: Literature Review of Factors Influencing Pain Sensation at the Injection Site. Adv Ther 36, 2986-2996 (2019). (Year: 2019).*
Buhler, Polyvinylpyrrolidone Excipients for Pharmaceuticals, ISBN 3-540-23412-8, (Year: 2005).*
Krenn et al., "Improvements in Solubility and Stability of Thalidomide upon Complexation with Hydroxypropyl-B-Cyclodextrin", Journal of Pharmaceutical Sciences, American Chemical Society and American Pharmaceutical Association, vol. 81, No. 7, Jul. 1, 1992, 5 pages.
International Search Report and Written Opinion for PCT/US2022/011572, dated May 4, 2022, 14 pages.
Blum; Journal of Clinical Oncology 2010, 28, 4919-4925. (Year: 2010).
Carlson; Annals of Internal Medicine 1983, 99, 823-833. (Year: 1983).
Chen; J Clin Oneal. 2011, 29, 1175-1181. (Year: 2011).
Eisen; British Journal of Cancer 2000, 82, 812-817. (Year: 2000).
Eriksson; Journal of Pharmacy and Pharmacology, 2000, 52, 807-817. (Year: 2000).
Franks; Lancet 2004, 363, 1802-1811. (Year: 2004).
Galustian; Expert Opinion on Pharmacotherapy 2009, 10, 125-133. (Year: 2009).
Gu; Molecular Pain 2010, 6, 64, 10 pages. (Year: 2010).
Kelleher, ChemioCare launches development of transdermal patch for multiple myeloma drug—lenalidomide. Proactive Investors. Apr. 23, 2019. 2 pages. Accessible at .proactiveinvestors.com/companies/news/218960/chemiocare-launches-development-of-transdermal-patch-for-multiple-myeloma-drug---lenalidomide-218960.html.

(Continued)

*Primary Examiner* — Amy L Clark
*Assistant Examiner* — Liyuan Mou
(74) *Attorney, Agent, or Firm* — Womble Bond Dickinson (US) LLP

(57) ABSTRACT

Provided are compositions comprising a stable solution of an immune-mediated inflammatory disease (IMID) agent, such as an immunomodulatory imide drug (IMiD) including, but not limited to, lenalidomide (LLD). More particularly, embodiments relate to stable solutions of IMiDs for parenteral use. Methods of preparing stable solutions of IMiDs are also provided. In some embodiments, methods of treating inflammatory disorders and cancer(s) by parenteral use of stable IMiD solutions, and formulations thereof, are provided.

6 Claims, 16 Drawing Sheets

(56) References Cited

OTHER PUBLICATIONS

Mandac et al., Lenalidomide induced good clinical response in a patient with multiple relapsed and refractory Hodgkin's lymphoma. J Hematol Oncol. May 28, 2010;3:20(1-3).
Pereira et al., Evaluation of the effects of thalidomide-loaded biodegradable devices in solid Ehrlich tumor. Biomed Pharmacother. Mar. 2013;67(2):129-32. Epub Sep. 18, 2012.
Pineda-Roman; Leukemia 2008, 22, 1419-1427. (Year: 2008).
Priyanka; Asian J Pharm Clin Res, Feb. 2019,12, 411-417. (Year: 2019).
Revlimid® Prescribing Information, revised Feb. 2017, 45 pages. (Year: 2017).
Schafer; Cellular Signalling 2014, 26, 2016-2029. (Year: 2014).
Weber; Cancer Control, 2003, 10, 375-383. (Year: 2003).
Waghule; Biomedicine and Pharmacotherapy 2019, 109, 1249-1258. (Year: 2019).

\* cited by examiner

STABLE SOLUTIONS OF IMMUNOMODULATORY IMIDE COMPOUNDS FOR PARENTERAL USE

RELATED APPLICATIONS

The present application claims priority to and the benefit of U.S. Provisional Patent Application No. 63/135,347, filed on Jan. 8, 2021, the entire contents of which are hereby incorporated by reference for all purposes.

TECHNICAL FIELD

The present subject matter generally relates to a composition comprising a stable solution of an immunomodulatory agent, such as immune-mediated inflammatory diseases (IMIDs) drugs including lenalidomide (LLD). More particularly, embodiments relate to a stable solution of LLD for parenteral use. Methods of preparing stable solutions of LLD and other immunomodulatory imide drugs (IMiDs) are also provided. In some embodiments, methods of treating inflammatory disorders and cancer by parenteral use of stable IMiD solutions, and formulations thereof, are provided. Surprisingly, the LLD solutions described herein exhibit superior LLD solubility and stability when compared with standard LLD solutions and formulations.

BACKGROUND

Immunomodulatory imide compounds include thalidomide and thalidomide analogues (collectively the thalidomide family of compounds), which possess pleiotropic anti-myeloma properties including immune-modulation, anti-angiogenic, anti-inflammatory and anti-proliferative effects. The thalidomide analogues include lenalidomide, pomalidomide, and iberdomide.

Lenalidomide (3-(4-amino-1-3-dihydro-1-oxo-2H-isoindol-2yl)-2,6-piperidinedione), as shown in Formula I below, is an FDA-approved drug which is available in the form of an oral capsule, as Revlimid®. Lenalidomide (LLD) is indicated, for example, for treatment of patients with: multiple myeloma (MM) in combination with dexamethasone; MM as maintenance following autologous hematopoietic stem cell transplantation (auto-HSCT); transfusion-dependent anemia due to low- or intermediate-1-risk myelodysplastic syndromes (MDS) associated with a deletion 5q abnormality with or without additional cytogenetic abnormalities; mantle cell lymphoma (MCL) whose disease has relapsed or progressed after two prior therapies, one of which included bortezomib; previously treated follicular lymphoma (FL) in combination with a rituximab product; or previously treated marginal zone lymphoma (MZL) in combination with a rituximab product. Revlimid® is available in an oral dosing form in strengths of 2.5 mg, 5 mg, 10 mg, 15 mg, 20 mg, and 25 mg.

Formula I

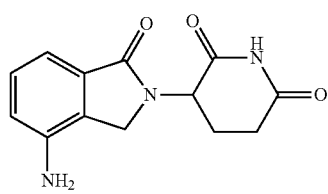

Pomalidomide (4-amino-2-(2,6-dioxopiperidin-3-yl)isoindoline-1,3-dione), shown as Formula II below, is also an FDA-approved drug, which is available in the form of oral capsules. Pomalidomide, is typically used, often in combination with dexamethasone, for patients with multiple myeloma who have received prior therapy (such as lenalidomide) and have demonstrated disease progression upon completion (or shortly thereafter) of the last therapy. Pomalidomide is available in an oral dosage form at strengths of 1 mg, 2 mg, 3 mg, and 4 mg.

Formula II

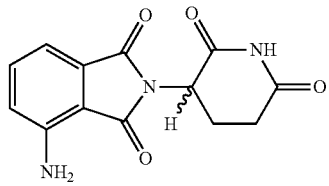

Thalidomide (2-(2,6-dioxopiperidin-3-yl)isoindole-1,3-dione) shown as Formula III below, is an FDA-approved drug, which is available in the form of oral capsules. Thalidomide is typically used, often in combination with dexamethasone, for the treatment of patients with newly diagnosed multiple myeloma. Thalidomide is available in an oral dosage form at strengths of 50 mg, 100 mg, 150 mg, and 200 mg.

Formula III

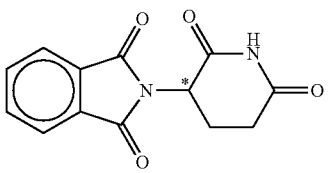

Iberdomide ((3S)-3-[7-[[4-(morpholin-4-ylmethyl)phenyl]methoxy]-3-oxo-1H-isoindol-2-yl]piperidine-2,6-dione), which is shown below as Formula V, is under development for treating refractory multiple myeloma.

Formula V

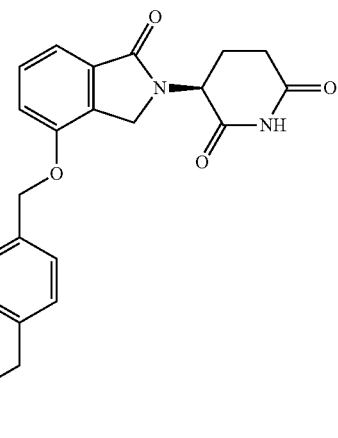

Lenalidomide (LLD)

LLD is disclosed in literature and various websites, such as www.pubchem.com, as purportedly exhibiting very slight water solubility, as provided for in prescribing information for Revlimid, Solubility in less acidic buffers is reported to range from about 0.4 to 0.5 mg/mL. Accordingly, lenalidomide was not reported to be chemically or physically stable in these solutions.

Recent scientific efforts have shown, for example, that in the range of physiologically acceptable pH range from about pH 3 to about pH 8, solubility of LLD may be limited to no more than about 0.4 mg/mL and dependent on storage conditions, may be as low as about 0.2 mg/mL in relative pH range from about pH 6.0 to about pH 7.0. Moreover, LLD is not chemically stable in solutions with or without the presence of buffers in the range from about pH 6.0 to about pH 7.0 and is significantly less chemically stable as pH range increases above 7.0 (e.g., basic conditions such as 0.1 NaOH would be expected to cause ~100% degradation). Solubility significantly decreases to about 0.0 mg/mL with increasing pH greater than about pH 7.0.

LLD has recently been reported to be subject to both basic hydrolysis and oxidation. LLD degrades into at least two (2) primary identified hydrolytic degradant peaks observed under chromatographic analysis and at least two (2) primary identified oxidation degradant peaks observed under the same chromatographic HPLC method.

Furthermore, LLD is known to have several primary related compounds that may constitute impurities in pharmaceutical compositions of LLD, as shown in Table 1.

Specifically, LLD exhibits predictable degradation under, for example, oxidative or hydrolytic conditions. LLD is relatively stable when exposed to acidic hydrolysis (HCl) but is susceptible to oxidation ($H_2O_2$) and basic hydrolysis (NaOH). For example, LLD is thought to degrade via the following degradation pathways:

Primary Basic Hydrolysis Pathway

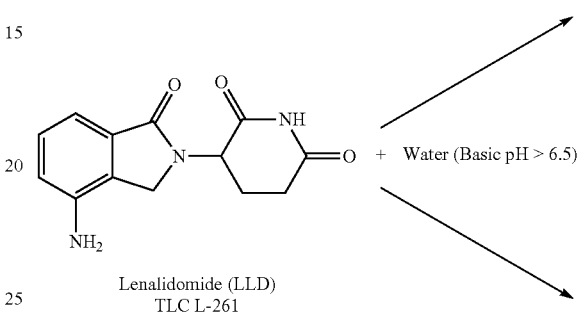

Lenalidomide (LLD)
TLC L-261

TABLE 1

LLD and Primary Related Compounds Nomenclature

| Compound Name | TLC* Compound Name | TLC* Code | CAS # | Formula | MW |
|---|---|---|---|---|---|
| Lenalidomide | Lenalidomide | L-261 | 191732-72-6 | $C_{13}H_{13}N_3O_3$ | 259.27 |
| 5-Amino-4-(4-amino-1-oxoisoindolin-2-yl)-oxopentanoic acid | LLD Imp 1 | L-264 | Not assigned | $C_{13}H_{15}N_3O_4$ | 277.28 |
| 5-Amino-2-(4-amino-1-oxoisoindolin-2-yl)-oxopentanoic acid | LLD Imp 2 | L-265 | 2197420-75-8 | $C_{13}H_{15}N_3O_4$ | 277.28 |
| Lenalidomide N-oxide ($NH_2 \rightarrow O$) | LLD Imp 9 | L-2613 | Not assigned | $C_{13}H_{13}N_3O_4$ | 275.27 |

*TLC Pharmaceutical Standards, http://www.tlcstandards.com/

LLD is also known to have several secondary and tertiary related compounds that may constitute impurities in pharmaceutical compositions, as shown in Table 2.

TABLE 2

Secondary and Tertiary Related Compounds Nomenclature

| Compound Name | TLC Compound Name | TLC Code | CAS # | Formula | MW |
|---|---|---|---|---|---|
| 2-(4-amino-1-oxoisoindolin-2-yl)-pentanedioic acid | LLD Imp 3 | L-266 | 295357-66-3 | $C_{13}H_{14}N_2O_5$ | 278.26 |
| 2-(4-Nitro-1-oxoisoindolin-2-yl)-pentanedioic acid | LLD Imp 12 | L-2617 | 295357-72-1 | $C_{13}H_{12}N_2O_7$ | 308.25 |
| 5-Amino-2-(4-nitro-1-oxoisoindolin-2-yl)-5-oxopentanoic acid | LLD Imp 13 | L-2618 | 874760-71-1 | $C_{14}H_{13}N_3O_4$ | 307.26 |
| 5-Amino-4-(4-nitro-1-oxoisoindolin-2-yl)-5-oxopentanoic acid | LLD Imp 14 | L-2619 | 1198299-72-7 | $C_{13}H_{13}N_3O_6$ | 307.26 |
| 3-(4-Nitro-1-oxoisoindolin-2-yl) piperidine-2,6-dione | LLD Imp 28 | L-263 | 827026-45-9 | $C_{13}H_{11}N_3O_5$ | 289.25 |

-continued

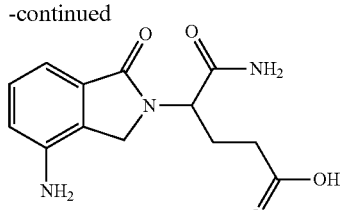

LLD Impurity 1
TLC L-264

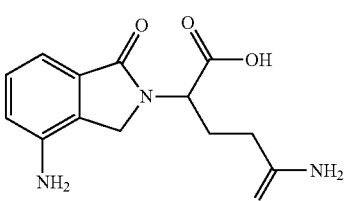

LLD Impurity 2
TLC L-265

Primary Oxidative Pathway

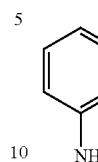

Lenalidomide (LLD)
TLC L-261

+ Oxygen (H₂O₂) →

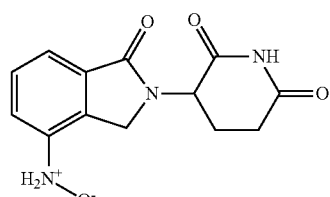

LLD Impurity 9
TLC L-2613

Secondary Basic Hydrolysis Pathway

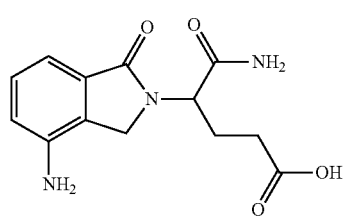

LLD Impurity 1
TLC L-264

+ Water (Basic pH > 6.5)

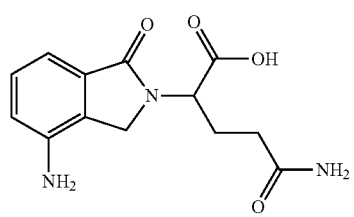

LLD Impurity 2
TLC L-265

Secondary Oxidative Pathway

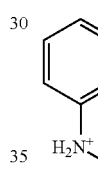

+ Oxygen (H₂O₂) →

LLD Impurity 9
TLC L-2613

LLD Impurity 28
TLC L-263

Tertiary Oxidative/Hydrolysis Pathways

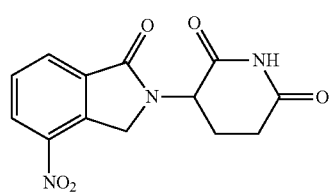

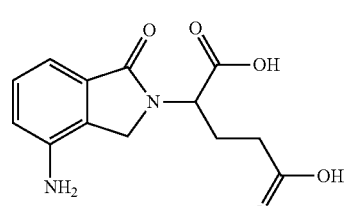

LLD Impurity 3
TLC L-266

TLC L-2617

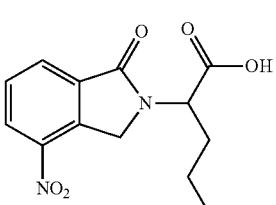

LLD Impurity 12

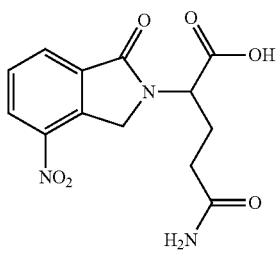

LLD Impurity 13

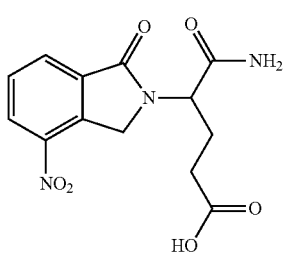

LLD Impurity 14

Without wishing to be bound by theory, it is believed that impurity 12 results from oxidation of impurity 3 or due to hydrolysis of impurities 13 or 14; impurity 13 results from oxidation of impurity 2 or due to hydrolysis of impurity 28; impurity 14 results from oxidation of impurity 1 or due to hydrolysis of impurity 28.

For the primary related compounds, it is believed that LLD impurity 1 is formed due to basic hydrolysis (preferred pathway); impurity 2 is formed due to basic hydrolysis (alternate pathway); impurity 9 is formed due to oxidation (preferred pathway) of the active pharmaceutical ingredient (API).

For the secondary related compounds, it is believed that LLD impurity 3 is formed due to basic hydrolysis of impurity 1 and impurity 2; impurity 28 is formed due to oxidation of impurity 9.

For the tertiary related compounds, it is believed that LLD impurity 12 is formed due to combination oxidation/hydrolysis from impurity 3, 13 and 14; impurity 13 is formed due to combination oxidation/hydrolysis from impurities 1 and 28; impurity 14 is formed due to combination oxidation/hydrolysis from impurities 2 and 28.

In drug development, a product is considered chemically stable when there is no or limited change in potency, and where the drug product is chemically stable with regards to written specification and International Conference on Harmonization of Technical Requirements for Registration of Pharmaceuticals for Human Use (ICH) guideline Q3B Impurities in New Drug Products for assessing total and individual impurities in new drug products when these products are held for up to 24 months at relative ICH storage conditions for frozen, refrigerated, room temperature and up to 6 months at accelerated conditions.

It is also believed that significant related compounds (>1.5%) Total Related Substances by peak area) form at T0 upon preparation of the LLD drug in standard solutions or formulations with both hydrolysis and oxidation events occurring at various levels. After only 48 hours at these ICH storage conditions, the formulations exhibit increases of these identified related substances up to >2.5% Total Related Substances and up to >10% Total Related Substances in higher pH ranges, such as pH 7.0 Phosphate Buffered Saline (PBS). With greater than 5% total related substances, there is a greater concern for toxicity, adverse events, generation of unknown degradation pathways, and secondary degradation events.

The currently approved LLD drug product is a solid oral dosage form presented as powder filled capsules. Thus, the drug is maintained in solid state, and the drug is less susceptible to degradation pathways by oxidation and or hydrolysis. In solid oral drug products, these degradation pathways can be mitigated by formulation, by desiccant and or by oxygen scavenger, individually and or in combination. See U.S. Pat. No. 7,465,800 to Jaworsky, et al., which describes a stable polymorph in crystalline form.

Injections, for subcutaneous, infusion, or other parenteral use are typically drug-in-solution in their simplest formulations and may also be emulsions, suspensions, microemulsions, nanoemulsions, microparticulates, and other dosage forms may be considered. For such dosage forms, there remains a need for a stable solution formulation of LLD. It is currently believed the formulation approach is challenging due to solubility of the LLD in solution <0.4 mg/mL with a target concentration in the range of 0.1 mg/mL to 20.0 mg/mL of the final drug product. It is also currently believed the formulation approach is challenging due to stability of LLD in solution where the API is unstable due to the formation of related substances from oxidative and hydrolytic degradation pathways and potentially other unknown degradation pathways or secondary reactions.

BRIEF SUMMARY

In a first aspect, a stable solution of an immunomodulatory imide drug (IMiD) that can be used to treat an immune-mediated inflammatory disease, such as LLD, is provided.

In some embodiments, the current technology is related to compositions comprising a stable concentrated solution of an IMiD in a polar aprotic solvent at a concentration ranging from about 0.1 mg/mL (0.01 wt. %) to about saturation, such as from about 0.2 mg/mL (0.02 wt. %) to about 200 mg/mL (20 wt. %), such as from about 0.5 mg/mL (0.05 wt. %) to about 100 mg/mL (10 wt. %), such as from about 1 mg/mL (0.1 wt. %) to about 60 mg/mL (6 wt. %). The combination of IMiD and polar aprotic solvent has proven to form a stable, true solution, free of crystalline particles. In this case, the starting polymorphic form is of no consequence in a true solution as the solute, IMiD Active Pharmaceutical Ingredient (API), is completely dissolved within the solvent, which, in this case, is a polar aprotic solvent that is substantially free of water. The polar aprotic solvent offers solubility and the solute is formulated well below the saturation level, which enhances the long-term stability of the solution. The polar aprotic solvent provides protection of the API from hydrolytic and/or oxidative reactions while in a most available and reactive state as the API is completely dissolved in the solution. It is expected to be stable in this form for up to 24 months under controlled conditions.

In other embodiments, the composition comprising a stable solution of an IMiD and a polar aprotic solvent comprises a polar aprotic solvent selected from n-methyl-2-pyrrolidone (NMP), 2-pyrrolidone (2-pyrol), dimethyl sulfoxide (DMSO), dimethylformamide (DMF), dimethylacetamide (DMAc), acetone, acetonitrile (ACN), tetrahydrofuran (THF), or others. In some embodiments, the polar aprotic solvent is a pharmaceutically acceptable polar aprotic solvent. In some embodiments, the polar aprotic solvent is NMP. In other embodiments, the current technology is related to a final diluted composition comprising a stable solution of an IMiD and a polar aprotic solvent comprises NMP in an amount of between about 0.1 wt. % to about 99 wt. %, such as from about 0.5 wt. % to about 50 wt. %, such as from about 1 wt. % to about 25% wt. %. In other embodiments, the present technology is related to a concentrated composition comprising up to 99 wt. % NMP such that the concentrated composition contains from about 70 wt. % to about 99 wt. % of the polar aprotic solvent (e.g., NMP) and from about 10 mg/mL or about 1% wt. % up to about 300 mg/mL or 30 wt. % of the API (e.g., LLD)

A final dilution of the concentrated solution above in an appropriate vehicle (e.g., diluent) to yield a stable formulation for the duration of administration comprising a soluble povidone (PVP) polymer having a pharmaceutically acceptable buffer with a pH range from about 3.0 to about 7.0 in the final composition is also described. In some embodiments, the IMiD is selected from LLD, thalidomide, pomalidomide, iberdomide, or a combination thereof. In other embodiments, the compositions include LLD in the concentration of from about 0.01 mg/mL (0.001 wt. %) to about saturation, such as from about 0.05 mg/mL (0.005 wt. %) to about 100.0 mg/mL (10 wt. %), such as from about 0.1 mg/mL (0.01 wt. %) and 20.0 mg/mL (2 wt. %) at an acceptable physiological pH in the final composition for administration.

In some embodiments, the compositions include a soluble povidone polymer that is a water-soluble polymer. In other embodiments, the polymer comprises polyvinylpyrrolidone (PVP) or copolymers thereof. In some embodiments, the PVP comprises an average molecular weight of about 2,000 to about 1,200,000, such as from about 2,000 to about 54,000, and the concentration of the soluble povidone polymer in the composition can range from about 0.1 wt. % to about 25 wt. %, such as from about 0.2 wt. % to about 20 wt. %, such as from about 0.4 wt. % to about 10 wt. %. In some embodiments, the soluble povidone polymer can have an average molecular weight ranging from about 1,000 to about 18,000, such as from about 1,500 to about 16,000, such as from about 2,000 to about 14,000 (e.g., Kollidon K-12, Kollidon K-17). Further, the concentration of the soluble povidone polymer when such molecular weights are used can range from about 2 wt. % to about 25 wt. %, such as from about 4 wt. % to about 20 wt. %, such as from about 6 wt. % to about 10 wt. %. In still other embodiments, the soluble povidone polymer can have an average molecular weight ranging from about 20,000 to about 100,000, such as from about 22,000 to about 90,000, such as from about 24,000 to about 80,000 (e.g., Kollidon K-25, Kollidon K-30, Kollidon VA64), and the concentration of the soluble povidone polymer in the composition can range from about 0.1 wt. % to about 10.0 wt. %, such as from about 0.5 wt. % to about 8 wt. %, such as from about 1 wt. % to about 6 wt. %.

In some embodiments, the present technology is related to formulations comprising an IMiD, such as LLD, wherein the IMiD is resistant to degradation. In some embodiments, the IMiD is resistant to hydrolytic or oxidative degradation, including forced degradation of acidic, basic or oxidative conditions.

In other embodiments, the current technology is related to stable solutions of IMiD and a polymer wherein the solution comprises a formulation for topical, oral, transdermal, or parenteral administration (intramuscular, intravenous, subcutaneous, depot, implant, intraarterial, intraperitoneal, or infusion or others), and preferably by subcutaneous infusion.

In other embodiments, the stable solutions of IMiD and a polymer further comprise an excipient or combination of excipients. In some embodiments, the excipient is selected from the group consisting of solvents, solubilizers, diluents, suspending agents, dispersing agents, gelling agents, polymers, biodegradable polymers, penetration enhancers, plasticizers, pH adjusting agents, buffering agents, pH stabilizers, emulsifying agents, auxiliary emulsifying agents, surfactants, suspending agents, stabilizers, preservatives, chelating agents, complexing agents, emollients, humectants, demulcents, skin irritation reducing agents, antioxidants, oxidants, tackifiers, fillers, and volatile chemicals.

In another aspect, the current technology is related to a composition comprising a stable solution of an IMiD, a soluble povidone polymer, and a polar aprotic solvent in a concentrate or in final diluted composition for administration. In some embodiments the stable solution of an IMiD with a polymer and a polar aprotic solvent comprises an IMiD selected from lenalidomide, thalidomide, pomalidomide, and or iberdomide.

In some embodiments, the composition comprising a stable solution of an IMiD, a soluble povidone polymer, and a polar aprotic solvent comprises lenalidomide at a concentration ranging from about 0.01 mg/mL (0.001 wt. %) to about saturation or about 300 mg/mL (30% wt. %), such as from about 0.1 mg/mL (0.01 wt. %) to about 100.0 mg/mL (10% wt. %), such as from about 0.2 mg/mL (0.02 wt. %) to about 20.0 mg/mL (2 wt. %) at physiological pH in the final composition for administration. Further, the soluble povidone polymer can be present in the concentrated solution from about 0.01 mg/mL (0.001 wt. %) to about 500 mg/mL (50% wt. %), such as from about 0.1 mg/mL (0.01 wt. %) to about 300 mg/mL (30% wt. %), such as from about 0.2 mg/mL (0.02 wt. %) to about 100 mg/mL (10% wt. %). The polar aprotic solvent can be present as the balance of the solution at a concentration ranging from about 20% wt. % to about 99.998% wt. %, such as from about 60 wt. % to about 99.98 wt. %, such as from about 88 wt. % to about 99.96 wt. %.

In some embodiments, the composition comprising a stable solution of an IMiD, a soluble povidone polymer, and a polar aprotic solvent comprises a water-soluble polymer.

In some embodiments, the composition comprising a stable solution of an IMiD, a soluble povidone polymer, and a polar aprotic solvent comprises polyvinylpyrrolidone (PVP) or copolymers thereof. In some embodiments, the PVP comprises an average molecular weight of about 2,000 to about 1,200,000. In other embodiments, the PVP comprises an average molecular weight of about 2,000 to about 54,000. In some embodiments, the concentration of PVP in composition is from about 0.1 wt. % to about 25.0 wt. %, such as from about 0.2 wt. % to about 20 wt. %, such as from about 0.4 wt. % to about 10.0 wt. %.

In other embodiments, the composition comprising a stable solution of an IMiD, a soluble povidone polymer, and a polar aprotic solvent comprises, a polar aprotic solvent selected from n-methyl-2-pyrrolidone (NMP), 2-pyrrolidone (2-pyrol), dimethyl sulfoxide (DMSO), dimethylformamide (DMF), dimethylacetamide (DMAc), acetone, acetonitrile (ACN), tetrahydrofuran (THF), or others. In some embodiments, the polar aprotic solvent is a pharmaceutically acceptable polar aprotic solvent. In some embodiments, the polar aprotic solvent is NMP. In other embodiments, the current technology is related to a final diluted composition comprising a stable solution of an IMiD, a soluble povidone polymer, and a polar aprotic solvent comprises NMP at a concentration ranging from about 0.1 wt. % to about 50 wt. %, such as from about 1 wt. % to about 44 wt. %. In other embodiments, the present technology is related to a concentrated composition comprising a polar aprotic solvent (e.g., NMP) at a concentration of up to about 99 wt. %. PVP may be present up to its solubility limit in the polar aprotic solvent, (i.e., up to about 30 wt. % in concentrate and dependent on the molecular weight (MW) of the PVP), such that the concentrated composition is mostly NMP (e.g., present at a concentration ranging from about 70 wt. % to about 99 wt. %) and the API, such as LLD, (up to about 300 mg/mL or 30 wt. %). PVP, if present in the concentrated entry solution, may be incorporated up to the solubility limit in the polar aprotic solvent (up to about 30 wt. %), such that the concentrated composition is mostly NMP (e.g., 50 wt. % to 99 wt. %), PVP (1 wt. % to 50 wt. %) and the active pharmaceutical ingredient, such as LLD, (up to about 30 wt. %).

In some embodiments, the composition comprising a stable solution of an IMiD, a soluble povidone polymer, and a polar aprotic solvent comprises an IMiD that is resistant to degradation, such as hydrolytic or oxidative degradation, and/or forced degradation under acidic, basic or oxidative conditions.

In some embodiments the composition comprising a stable solution of an IMiD, a soluble povidone polymer, and a polar aprotic solvent comprises a formulation for topical, oral, transdermal, or parenteral administration (intramuscular, intravenous, subcutaneous, depot, implant, intraarterial, intraperitoneal, or infusion or others), and preferably by subcutaneous infusion. In some embodiments, the formulation further comprises an excipient or combination of excipients. In some embodiments, the excipient is selected from the group consisting of solvents, solubilizers, diluents, suspending agents, dispersing agents, gelling agents, polymers, biodegradable polymers, penetration enhancers, plasticizers, pH adjusting agents, buffering agents, pH stabilizers, emulsifying agents, auxiliary emulsifying agents, surfactants, suspending agents, stabilizers, preservatives, chelating agents, complexing agents, emollients, humectants, demulcents, skin irritation reducing agents, antioxidants, oxidants, tackifiers, fillers, and volatile chemicals.

In another aspect, methods of preparing stable IMiD solutions, such as stable LLD solutions, and formulations thereof are provided.

In some embodiments, the present technology provides methods for preparing a composition comprising a stable solution of LLD and a soluble povidone polymer, comprising adding the LLD to a solution of povidone polymer at an appropriate physiological pH. In some embodiments, the method comprises PVP as the povidone polymer. In other embodiments, the method produces a stable solution comprising from about 0.1 mg/mL (0.01 wt. %) to about 20.0 mg/mL (2 wt. %) LLD at physiological pH.

In other embodiments, the methods described herein provide LLD that is resistant to hydrolytic and/or oxidative forced degradation when exposed to acidic, basic or oxidative conditions. In some embodiments, the methods described herein provide a stable solution of LLD and a polymer in formulation for parenteral administration.

In another aspect, the current technology is related to a method of preparing a concentrated composition comprising a stable solution of an IMiD, such as LLD, polar aprotic solvent, a povidone; comprising adding the LLD to a solution of povidone polymer and polar aprotic solvent. In some embodiments, the concentrated composition is substantially free of water. In some embodiments, the concentrated composition comprises PVP. In other embodiments, the concentrated composition comprises n-methyl-2-pyrrolidone (NMP).

In some embodiments, the concentrated composition, comprises PVP and LLD that are solubilized by the polar aprotic solvent. In other embodiments, the concentrated composition comprises additional pharmaceutically acceptable excipients that are soluble in the concentrated solution of LLD, PVP, and NMP.

In some embodiments, the concentrated composition comprises a solubilized IMiD in a concentration from about 0.1 mg/mL (0.1 wt. %) to about 100 mg/mL (10 wt. %) LLD. In other embodiments, the PVP is present and solubilized in a concentration ranging from about 0.1 wt. % to about 50 wt. %. In other embodiments, the NMP is present in a concentration ranging from about 50 wt. % to about 99.8 wt. %.

In some embodiments, the concentrated composition comprises an IMiD that is resistant to hydrolytic and/or oxidative forced degradation when exposed to acidic, basic or oxidative conditions.

In some embodiments, the current technology is related to stable solutions of IMiDs, such as LLD, a polymer, and polar aprotic solvent in a concentrated formulation to be diluted for parenteral administration. In some embodiments, the stable solution comprises PVP, a polar aprotic solvent, and from about 0.1 mg/mL (0.01 wt. %) to about 100.0 mg/mL (10 wt. %) LLD in a concentrated formulation to be diluted for parenteral administration with an appropriate buffer solution. In other embodiments, the solution of PVP, polar aprotic solvent, and from about 0.1 mg/mL (0.01 wt. %) to about 20 mg/mL (2 wt. %) LLD is diluted to volume with appropriate buffer to achieve a stable solution within the physiological pH range of from about 4.0 to about 7.0, such as from about 5.0 to about 6.5. In some embodiments, the current technology is related to stable solutions of IMiDs, such as LLD, wherein the final concentration ranges are about 0.1 wt. % to about 25 wt. %, such as from about 0.4 wt. % to about 10 wt. % for PVP; and from about 0.1 wt. % to about 44%, such as from about 0.5 wt. % to about 20 wt. % for NMP.

In some embodiments, the current technology is related to stable solutions of IMiDs, such as LLD and polar aprotic solvent in a concentrated formulation to be diluted for parenteral administration. In some embodiments, the stable solution comprises polar aprotic solvent and about 0.1 mg/mL (0.01 wt. %) to about 100.0 mg/mL (10 wt. %) LLD in a concentrated formulation to be diluted for parenteral administration with an appropriate buffer solution. The diluent or appropriate buffer solution is formulated to accommodate the NMP:LLD concentrate at a ratio ranging from about 1:1 to about 1:50, such as from about 1:2 to about 1:30, such as from about 1:5 to about 1:26. In some embodiments, the current technology of the diluent solution comprises PVP, buffering reagents, and water for injection at physiological pH ranging from about 3 to about 6. The PVP in this diluent solution is present at a concentration ranging from about 0.1 wt. % to about 25 wt. %, such as from about 0.2 wt. % to about 20 wt. %, such as from about 0.4 wt. % to about 10 wt. %.

Also provided are methods of treating diseases or conditions which LLD is known to be capable of treating, including, for example, multiple myeloma, transfusion-dependent anemia due to low- or intermediate-1-risk myelodysplastic syndromes, mantle cell lymphoma, chronic lymphocytic leukemia, hematologic cancers, or solid tumor cancers, psoriatic arthritis, or cytokine release syndrome, wherein the method comprises continuous administration of the immunomodulatory imide compound to a subject in need of the treatment. In some embodiments, the method comprises administering the immunomodulatory imide compound continuously to a subject at a predetermined hourly rate for a predetermined number of days.

In another aspect, the current technology provides a method of treating an inflammatory disorder or cancer by parenteral administration of a formulation comprising a stable solution of an IMiD, such as LLD, and a polymer. In some embodiments, the method of treating comprises a stable solution comprising PVP and from about 0.1 mg/mL (0.01 wt. %) to about 20.0 mg/mL (2 wt. %) LLD at physiological pH. In other embodiments, the stable IMiD solutions are administered parenterally in the form of a formulation comprising the stable IMiD, such as stable LLD solution, and a pharmaceutically acceptable carrier.

In one particular embodiment, a composition that includes an immunomodulatory imide (IMiD) compound, a polar aprotic solvent, and a soluble povidone polymer is provided.

The composition can have a pH ranging from about 3.0 to about 7.0 prior to administration.

Further, the immunomodulatory imide (IMiD) compound can include lenalidomide, pomalidomide, iberdomide, or a combination thereof, the polar aprotic solvent can include n-methyl-2-pyrrolidone, 2-pyrrolidone, dimethyl sulfoxide, dimethylformamide, dimethylacetamide, acetone, acetonitrile, tetrahydrofuran, or a combination thereof, and the soluble povidone polymer can be water soluble and can include polyvinylpyrrolidone or copolymers thereof.

Additionally, the composition can have an osmolality ranging from about 250 mOsm/kg to about 1600 mOsm/kg.

In one embodiment, the composition can include an entry solution and a diluent solution, wherein the entry solution and the diluent solution are maintained separately prior to administration to a patient, at which time the entry solution and diluent solution are combined to form a final solution for administration to the patient. Further, the entry solution can include the immunomodulatory imide (IMiD) compound, the polar aprotic solvent, and optionally the soluble povidone polymer. In addition, the immunomodulatory imide (IMiD) compound can be present in the entry solution at a concentration ranging from about 0.05 wt. % to about 30 wt. %, the polar aprotic solvent can be present in the entry solution at a concentration ranging from about 60 wt. % to about 99.0 wt. %, and the soluble povidone polymer can be present in the entry solution at a concentration ranging from 0 wt. % to about 30 wt. %, based on the total weight of the entry solution.

Meanwhile, the diluent solution can include the soluble povidone polymer, a buffering system, water, and optionally the polar aprotic solvent. Further, the soluble povidone polymer can be present in the diluent solution at a concentration ranging from about 0.1 wt. % to about 10 wt. %, the buffering system can be present in the diluent solution at a concentration ranging from about 0.02 wt. % to about 10 wt. %, the water can be present in the diluent solution at a concentration ranging from about 56 wt. % to about 99.8 wt. %, and the polar aprotic solvent can be present in the diluent solution at a concentration ranging from 0 wt. % to about 10 wt. %, based on the total weight of the diluent solution.

Additionally, the buffering system can include citric acid and sodium bicarbonate. The citric acid can be present in the diluent solution at a concentration ranging from about 0.01 wt. % to about 5 wt. % and the sodium bicarbonate can be present in the diluent solution at a concentration ranging from about 0.01 wt. % to about 5 wt. %, based on the total weight of the diluent solution.

Further, the final solution can include the immunomodulatory imide (IMiD) compound, the polar aprotic solvent, the soluble povidone polymer, a buffering system, and water.

For example, the immunomodulatory imide (IMiD) compound can be present in the final solution at a concentration ranging from about 0.01 wt. % to about 1 wt. %, the polar aprotic solvent can be present in the final solution at a concentration ranging from about 0.1 wt. % to about 30 wt. %, the soluble povidone polymer can be present in the final solution at a concentration ranging from about 0.1 wt. % to about 10 wt. %, the buffering system can be present in the final solution at a concentration ranging from about 0.02 wt. % to about 10 wt. %, and the water can be present in the final solution at a concentration ranging from about 55 wt. % to about 99.8 wt. %, based on the total weight of the final solution.

Additionally, the buffering system can include citric acid and sodium bicarbonate. Further, the citric acid can be present in the final solution at a concentration ranging from about 0.01 wt. % to about 5 wt. % and the sodium bicarbonate can be present in the final solution at a concentration ranging from about 0.01 wt. % to about 5 wt. %, based on the total weight of the final solution.

Moreover, the soluble povidone polymer can have an average molecular weight ranging from about 20,000 to about 100,000, or can have an average molecular weight ranging from about 1,000 to about 18,000.

In addition, the composition can include a formulation for topical, oral, transdermal, or parenteral administration. The parenteral administration can be intramuscular, intravenous, subcutaneous, depot, intraarterial, intraperitoneal, infusion, or by implant administration. Moreover, the parenteral administration can be a subcutaneous infusion, where the subcutaneous infusion can be continuous, pulsatile, or intermittent with an uninterrupted drug supply from an external drug supply. Further, the external drug supply is not disconnected during the parenteral administration except when necessary to change or replenish the formulation or when treatment is completed as determined by a medical professional.

Additionally, the composition embodied above can include an excipient. The excipient can include a solvent, a solubilizer, a diluent, a suspending agent, a dispersing agent, gelling agent, polymer, penetration enhancer, plasticizer, pH adjusting agent, pH stabilizer, emulsifying agent, a cyclodextrin and derivatives thereof, a surfactant, a preservative, a chelating agent, a complexing agent, an emollient, a humectant, a demulcent, a skin irritation reducing agent, an antioxidant, an oxidant, a tackifier, a filler, a crystallization inhibitor, a volatile chemical, or a combination thereof.

Also contemplated is a method of administering the final solution as described above to a patient.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

DETAILED DESCRIPTION

Figure 1:
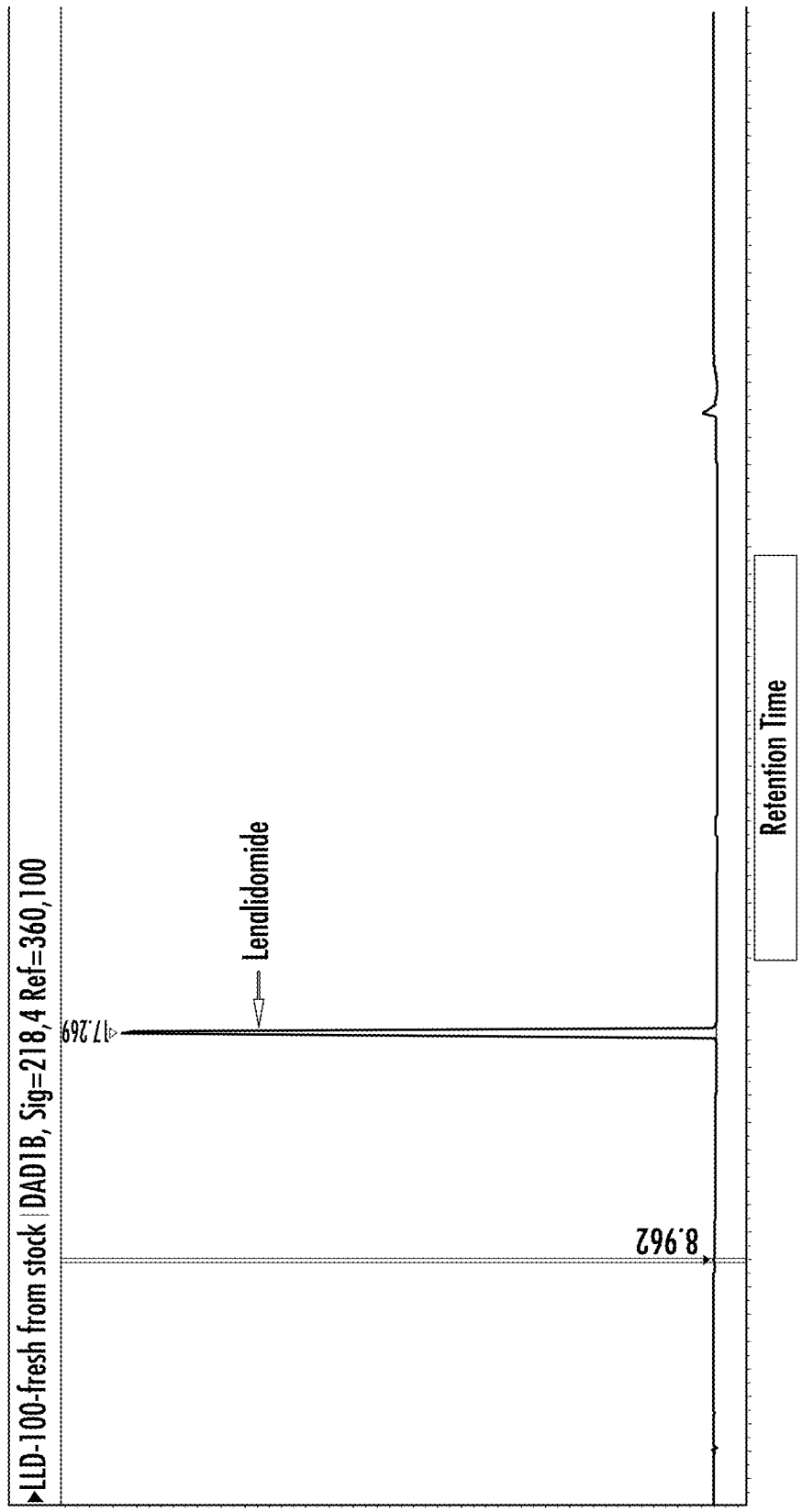
FIG. 1 is a high-performance liquid chromatography (HPLC) chromatogram of an LLD sample stored in a reference standard control solution at ambient room temperature.

As used herein, the term "pharmaceutically acceptable salts" includes acid addition salts or addition salts of free bases. The term "pharmaceutically acceptable salts" within its scope include each of all the possible isomers and their mixtures, and any pharmaceutically acceptable metabolite, bioprecursor and/or pro-drug, such as, for example, a compound which has a structural formula different from the one of the compounds recited or described, yet is directly or indirectly converted in vivo into such a compound upon administration to a subject, such as a mammal, and particularly a human being.

As used herein, the terms "subject" and "patient" are used interchangeably. As used herein, the term "patient" refers to an animal, preferably a mammal such as a non-primate (e.g., cows, pigs, horses, cats, dogs, rats etc.) and a primate (e.g., monkey and human), and most preferably a human. In some embodiments, the subject is a non-human animal such as a farm animal (e.g., a horse, pig, or cow) or a pet (e.g., a dog or cat). In a specific embodiment, the subject is an elderly human. In another embodiment, the subject is a human adult. In another embodiment, the subject is a human child. In yet another embodiment, the subject is a human infant.

As used herein, the term "active", "agent", or "therapeutic agent" refers to any molecule, compound, methodology and/or substance that is used for the prevention, treatment, management and/or diagnosis of a disease, disorder or condition.

As used herein, the term "effective amount" refers to the amount of a therapy or agent that is sufficient to result in the prevention of the development, recurrence, or onset of a disease or condition, the prevention, treatment, reduction or amelioration of one or more symptoms thereof, the enhancement or improvement of the prophylactic effect(s) of another therapy, the reduction of the severity or the duration of a disease or condition, the amelioration of one or more symptoms of a disease or condition, the prevention of the advancement of a disease or condition, the regression of a disease or condition or one or more of its symptoms, and/or the enhancement or improvement of the therapeutic effect(s) of another therapy.

As used herein, the phrase "pharmaceutically acceptable" means approved by a regulatory agency of the federal or a state government, or listed in the U.S. Pharmacopeia, European Pharmacopeia, Chinese Pharmacopeia, or other generally recognized pharmacopeia for use in animals, and more particularly, in humans.

As used herein, the term "treat", "treating", "treatment", or "therapy" of a disease or disorder refers to ameliorating the disease or disorder; for example slowing, arresting or reducing the disease, its development, or one or more clinical symptoms thereof; the term also refers to alleviating or ameliorating one or more physical parameters, whether or not discernible by the patient; the term also refers to physically and/or physiologically modulating the disease or disorder (e.g. by stabilization of a discernible symptom and/or physical parameter).

As used herein, the term "prevention" of a disease or disorder refers to the administration of the compounds of the invention to a subject before any symptoms of that disease or disorder are apparent.

As used herein, a patient or subject is "in need of" a treatment if the patient or subject would benefit biologically, medically or in quality of life from such treatment.

The term "analog," "derivative" or "derivatized" as used herein includes chemical modification of a compound, or pharmaceutically acceptable salts thereof or mixtures thereof. That is, a "derivative" may be a functional equivalent of a compound which is capable of inducing the functional activity of the compound in a given subject or application.

As used herein, the terms "composition" and "formulation" may be used interchangeably, unless otherwise indicated. Generally, a formulation may be used as a stand-alone stable solution of LLD for parenteral administration.

As used herein, the term "a," "an," "the" and similar terms used in the context of the present invention are to be construed to cover both the singular and plural unless otherwise indicated herein or clearly contradicted by the context. The use of any and all examples, or exemplary language (e.g., "such as", "for example", "illustrative", "e.g.,") provided herein is intended merely to better illustrate the invention and is not intended to limit the scope of the invention.

As used herein, the term "therapeutic agent" refers to any molecule, compound, and/or substance that is used for the purpose of treating and/or managing a disease or disorder.

As used herein, the terms "therapies" and "therapy" can refer to any method(s), composition(s), and/or agent(s) that can be used in the prevention, treatment and/or management of a disease or condition, or one or more symptoms thereof. In certain embodiments, the terms "therapy" and "therapies" refer to small molecule therapy.

As used herein, the term "entry solution (ES)" refers to a formulation of the currently described compositions that is formulated as a concentrate to initiate dissolution of insoluble API at a concentrated level for dilution in a finished dosage form. In some embodiments, an ES is not intended to constitute the final dosage form. In some embodiments, an ES is a true solution. In some embodiments, an ES is diluted to form the final dosage formulation.

As used herein, the term "diluent solution (DS)" refers to a formulation of the current technology formulated as a solution designed to dilute the concentrated entry solution. In some embodiments, a DS is free of API. In some embodiments, a DS is a true solution.

As used herein, the term "finished dosage form" or "final drug product" or "finished drug product (FDP)" or the "final solution" refers to a formulation of the current technology comprising ES that has been diluted with DS to produce a final composition comprising appropriate concentrations of all components for use and/or administration. For example, in some embodiments, 1 mL of ES may be combined with 25 mL DS to produce a final volume of 26 mL of a finished drug product.

Formulations

The current technology is related, in part, to the use of NMP and PVP in the presence of LLD to provide increased solubility and surprising mitigation of LLD degradation. For example, hydrolytic and oxidative degradation under forced degradation conditions (such as aprotic solvent, ACN, in the presence of water solutions, and protic solvent, Isopropyl Alcohol (IPA), in the presence of water solutions)

The present technology also demonstrates that the molecular weight of PVP will have more protective capabilities from about 28 k to about 70 k (Kollidon K-25, K-30, VA64) in concentrations ranging from about 0.1 wt. % to about 10 wt. %, such as from about 0.5 wt. % to about 8 wt. %, such as from about 1 wt. % to about 6 wt. %. In some embodiments, higher concentrations of PVP may be preferred, however, parenteral toxicity may become a rate limiting factor with higher molecular weight PVP.

The present technology provides evidence that the lower molecular weight PVPs (Kollidon K-12 and K-17) offer similar level of protection against hydrolytic and oxidative degradation under forced degradation conditions. However, higher concentrations of lower molecular weight PVPs, such as concentrations ranging from about 2 wt. % to about 25 wt. %, such as from about 4 wt. % to about 20 wt. %, such as from about 6 wt. % to about 10 wt. %, have shown protective stability comparable to lower concentrations of PVP mid-MW grades (Kollidon K-25, K-30 and VA64). Moreover, the highest molecular weight (Kollidon K-90) was determined to not be as protective against hydrolysis. These findings demonstrate to unpredictability of the art related to producing stable solutions of IMiDs, such as LLD.

Accordingly, Table 3 summarizes some of the findings of the present technology related to formulations comprising LLD and particular Kollidon grades, reported MW ranges of given grades, experimental pH of lab-made solutions of polymers in DI water, and a rank order of utility for protection of LLD degradation in presence of specified grade of Kollidon (1% polymer loading in DI water).

TABLE 3

Hydrolysis and Oxidation Inhibition of PVP water based-solutions

| Grade | MW Range | pH (1% Solution) | Hydrolysis Inhibition Rank Order | Oxidation Inhibition Rank Order |
| --- | --- | --- | --- | --- |
| Kollidon K-12 (parenteral) | 2 k-3 k | 4.63 | 6 | 1 |
| Kollidon K-17 (parenteral) | 7 k-11 k | 4.64 | 5 | 1 |
| Kollidon K-25 | 28 k-34 k | 4.00 | 2 | 1 |
| Kollidon K-30 | 44 k-54 k | 4.10 | 1 | 1 |
| Kollidon VA64 | 45 k-70 k | 4.51 | 3 | 2 |
| Kollidon K-90 | 1000 k-1500 k | 5.68 | 4 | 3 |

*BASF manufactures each grade of PVP as Kollidon ® in both a standard grade and low peroxide grade (PF) or (LP).

Additionally, the present technology provides utilization of a diluent solution with an osmolality suitable for a parenteral drug product in equilibrium with human blood (e.g., about 280 mOs/kg to about 300 mOs/kg). For example, typical buffer systems may be utilized to achieve and maintain a stable pH range from about 3.0 to about 7 such as from about 3.5 to about 6.5, such as from about 4 to about 6

Buffer systems of the current technology may include bicarbonate, phosphate, saline, citrate, succinate, histidine, acetate, or other suitable parenteral buffers. In one embodiment, a preferred buffer system can include citric acid monohydrate and sodium bicarbonate. Sodium chloride was found to be a suitable salt for osmolality adjustment, as needed.

It has been found that increasing the concentration of lower molecular weight povidone (Kollidon K-12, Kollidon K-17) up to about 10 wt. % in a water-based solution was viable to protect lenalidomide substantially from oxidation and significant improvement in hydrolytic stability was also observed.

Further, it has also been found that colligative properties of NMP have a significant impact on the osmolality of the water-based solution, and PVP has a negligible impact on osmolality. Specifically, as the concentration of NMP increases, it has been found that the osmolality increases at a much higher rate compared to increasing the concentration of PVP. As such, the specific concentrations of the polar aprotic solvent (e.g., NMP) and the soluble povidone polymer (e.g., PVP) and their respective ratios are critical to obtaining a suitable osmolality ranging from about 250 mOsm/kg to about 1600 mOsm/kg, such as from about 300 mOsm/kg to about 1300 mOsm/kg, such as from about 400 mOsm/kg to about 1200 mOsm/kg.

The current technology also considers other excipients for inclusion in the provided stable solutions that may be shown to be useful and may include, but not be limited to, antioxidants, other solubility enhancers, humectants, preservatives, bulking agents or other excipients used in combination with PVP and LLD to assist in stability, solubility or preservation of the formulation.

In some embodiments of the present technology, order of addition of ingredients to prepare solutions is of primary importance to maintain stability of the API. For example, in some embodiments, LLD must be brought into solution by a polar aprotic solvent with or without PVP, hereafter referred to as entry solution(s). In other embodiments, additives soluble in NMP may be incorporated, such as Citric acid monohydrate and or polyethylene glycol. In some embodiments, diluent is added at time of administration to prepare the final drug product to adjust pH and osmolality.

In other embodiments, final product concentrations of the stable solutions of IMiD of the present technology may be prepared as follows. For example, a bulk concentrate or entry solution (ES) may be prepared by adding an immunomodulatory compound (e.g., LLD) at a concentration ranging from about 0.05 wt. % to about 30 wt. %, such as from about 0.1 wt. % to about 20 wt. %, such as from about 1 wt. % to about 5 wt. % to a polar aprotic solvent (e.g., NMP) at a concentration ranging from about 60 wt. % to about 99.9 wt. %, such as from about 80 wt. % to about 99.25 wt. %, such as from about 95 wt. % to about 99 wt. % based on the total weight of the entry solution. Further, the ratio of the polar aprotic solvent to the immunomodulatory compound can range from about 99:1 to about 50:50, such as from about 98:2 to about 80:20, such that the immunomodulatory compound (e.g., LLD) is soluble in the polar aprotic solvent (e.g., NMP). For example, a bulk concentrate may be prepared by adding LLD up to about 1 mg/mL (0.1 wt. %), such as up to about 5 mg/mL (0.5 wt. %), such as up to about 6.5 mg/mL (0.65 wt. %), such as up to about 10 mg/mL (1 wt. %), such as up to about 13 mg/mL (1.3 wt. %), such as up to about 15 mg/mL (1.5 wt. %), such as up to about 19.5 mg/mL (1.95 wt. %), such as up to about 20 mg/mL (2 wt. %), such as up to about 25 mg/mL (2.5 wt. %), such as up to about 30 mg/mL (3 wt. %), such as up to about 35 mg/mL (3.5 wt. %), such as up to about 40 mg/mL (4 wt. %), such as up to about 45 mg/mL (4.5 wt. %), such as up to about 50 mg/mL (5 wt. %), such as up to about 55 mg/mL (5.5 wt. %), such as up to about 60 mg/mL (6 wt. %), such as up to about 65 mg/mL (6.5 wt. %), such as up to about 70 mg/mL (7 wt. %), such as up to about 75 mg/mL (7.5 wt. %), such as up to about 80 mg/mL (8 wt. %), such as up to about 85 mg/mL (8.5 wt. %), such as up to about 90 mg/mL (9 wt. %), such as up to about 95 mg/mL (9.5 wt. %), or such as up to about 100 mg/mL (10 wt. %), in NMP:LLD ratios ranging from about 99:1 to about 50:50, more preferably from about 98:2 to about 80:20 such that the LLD is soluble in NMP.

Further, although not required, the entry solution (ES) may contain a soluble povidone polymer (e.g., PVP or povidone) in an amount ranging from 0 wt. % to about 30 wt. %, such as from about 0.1 wt. % to about 15 wt. %, such as from about 0.2 wt. % to about 10 wt. % based on the total weight of the entry solution.

A diluent solution (DS), which is essentially free of the immunomodulatory compound, can also be prepared for combining with the entry solution (ES) to form the final solution or composition for delivery to a patient. Although not required, the diluent solution can include a polar aprotic solvent (e.g., NMP) ranging from 0 wt. % to about 10 wt. %, such as from about 0.1 wt. % to about 8 wt. %, such as from about 0.2 wt. % to about 6 wt. % based on the total weight of the diluent solution.

The diluent solution can also include a soluble povidone polymer (e.g., PVP or povidone, in an amount ranging from about 0.1 wt. % to about 10 wt. %, such as from about 1 wt. % to about 9 wt. %, such as from about 2 wt. % to about 8 wt. % based on the total weight of the diluent solution.

In addition, the diluent solution can include a buffering system that is present at a concentration ranging from about 0.02 wt. % to about 10 wt. %, such as from about 0.02 wt. % to about 4 wt. %, such as from about 0.4 wt. % to about 1.6 wt. %, such as from about 0.6 wt. % to about 1.2 wt. % based on the total weight of the diluent solution. The buffering system can include citric acid at a concentration ranging from about 0.01 wt. % to about 5 wt. %, such as from about 0.01 wt. % to about 2 wt. %, such as from about 0.2 wt. % to about 0.8 wt. %, such as from about 0.3 wt. % to about 0.6 wt. % based on the total weight of the diluent solution. The buffering system can further include isotonic solutions of neutralizing solutions, preferably of sodium bicarbonate with or without sodium chloride without further pH adjustment in concentrations from about 0.01 wt. % to 5 wt. % for each material maintaining osmolality between about 300 mOsm/kg to about 600 mOsm/kg, however, the range of osmolality may also range from about 250 mOsm/kg to about 1600 mOsm/kg, such as from about 300 mOsm/kg to about 1300 mOsm/kg, such as from about 400 mOsm/kg to about 1200 mOsm/kg. For instance, the buffering system in the diluent solution can include citric acid at the concentrations described above and may also include sodium bicarbonate at a concentration ranging from about 0.01 wt. % to about 5 wt. %, such as from about 0.01 wt. % to about 2 wt. %, such as from about 0.2 wt. % to about 0.8 wt. %, such as from about 0.3 wt. % to about 0.6 wt. % based on the total weight of the diluent solution.

Lastly, the diluent solution can include water in an amount to bring the total concentration up to 100 wt. %. Thus, the concentration of the water in the diluent solution can range from about 56 wt. % to about 99.8 wt. %, such as from about 80 wt. % to about 98 wt. %, such as from about 84 wt. % to about 96 wt. %, such as from about 88 wt. % to about 94 wt. % based on the total weight of the diluent solution.

Once the entry solution and the diluent solution are combined to form the final solution for delivery to a patient, where it is understood that the solutions maintained separately (e.g., as separate vials) until ready for use, the resulting concentrations of each component can be determined as described below. Specifically, the immunomodulatory agent (e.g., LLD) can be present in an amount ranging from about 0.01 wt. % to about 1 wt. %, such as from about 0.02 wt. % to about 0.9 wt. %, such as from about 0.03 wt. % to about 0.8 wt. % based on the total weight of the final solution.

Further, the polar aprotic solvent can be present in the final solution in an amount ranging from about 0.1 wt. % to about 30 wt. %, such as from about 1 wt. % to about 20 wt. %, such as from about 2.5 wt. % to about 15 wt. % based on the total weight of the final solution.

Additionally, the soluble povidone polymer can be present in the final solution in an amount ranging from about 0.1 wt. % to about 10 wt. %, such as from about 1 wt. % to about 9 wt. %, such as from about 2 wt. % to about 8 wt. % based on the total weight of the final solution.

In addition, the buffering system can be present at a concentration ranging from about 0.02 wt. % to about 10 wt. %, such as from about 0.02 wt. % to about 4 wt. %, such as from about 0.4 wt. % to about 1.6 wt. %, such as from about 0.6 wt. % to about 1.2 wt. % based on the total weight of the final solution. Further, it is to be understood that the buffering system can include citric acid at a concentration ranging from about 0.01 wt. % to about 5 wt. %, such as from about 0.01 wt. % to about 2 wt. %, such as from about 0.2 wt. % to about 0.8 wt. %, such as from about 0.3 wt. % to about 0.6 wt. % based on the total weight of the final solution, and can also include sodium bicarbonate can be present at a concentration ranging from about. 0.01 wt. % to about 5 wt. %, such as from about 0.01 wt. % to about 2 wt. %, such as from about 0.2 wt. % to about 0.8 wt. %, such as from about 0.3 wt. % to about 0.6 wt. % based on the total weight of the final solution.

The final solution may also include water in an amount ranging from about 55 wt. % to about 99.8 wt. %, such as from about 65 wt. % to about 95 wt. %, such as from about 75 wt. % to about 90 wt. % based on the total weight of the final solution.

In some embodiments, the final solution can be a composition that includes a stable solution of the immunomodulatory compound, the polar aprotic solvent, and the soluble povidone polymer can be prepared by either adding the immunomodulatory compound to a solution of the soluble povidone polymer and the polar aprotic solvent or by adding the immunomodulatory compound to the polar aprotic solvent. Then, to the resulting stable solution (e.g., the concentrated or entry solution) containing the immunomodulatory compound and the polar aprotic solvent with or without the addition of the soluble povidone polymer, which is substantially free of water, a diluent solution containing the soluble povidone polymer at an appropriate physiological pH and one or more excipients can be added to the entry solution. The resulting final solution is resistant to hydrolytic and/or oxidative forced degradation when exposed to acidic, basic or oxidative conditions.

Regardless of the particular manner in which the composition or final solution for delivery to the patient is formed or prepared, the administration to the patient can be topical, oral, transdermal, or parenteral administration. Further, the parenteral administration can be intramuscular, intravenous, subcutaneous, depot, implant, intraarterial, intraperitoneal, or infusion administration. In addition, when the parenteral administration is subcutaneous, the subcutaneous infusion is continuous, pulsatile, or intermittent with an uninterrupted drug supply. Additionally, whether the parenteral administration is continuous, pulsatile, or intermittent, it is to be understood that the external drug supply is not disconnected during the parenteral administration except when necessary to change or replenish the formulation or when treatment is completed as determined by a medical professional. Moreover, the external drug supply can include an ambulatory pump with an infusion line and catheter assembly that is affixed to the patient and can be subject for subcutaneous administration within a healthcare establishment. In other embodiments, the external drug supply can include a wearable patch pump in which the final solution is filled into a device that can be temporarily affixed to the patient via an adhesive or other means to adhere the patch pump to the patient or subject.

In some embodiments, formulations for entry solutions (ES), diluent solutions (DS) and final drug product solutions as discussed above are provided by Tables 4-6 which demonstrate that entry solutions comprise LLD and NMP, with or without PVP and/or citric acid monohydrate. For example, some embodiments include ES #1 that comprises LLD, PVP, NMP and citric acid monohydrate. Other embodiments include ES #2 that comprises LLD, PVP and NMP. Additional embodiments include ES #3 that comprises LLD and NMP. These formulations allow manipulation of either the ES or DS to accommodate the most stable dilution schema for LLD finished dosage forms.

Solubility work was further evaluated to determine LLD solubility in what later proved to be appropriate excipients for use in a solution product, such as povidone and Pharmasolve (n-methyl-2-pyrrolidone). These materials conform to a like-dissolves-like solubility. Acetonitrile was also evaluated as a polar aprotic solvent to assess solubility. Organic volatile solvents were assessed, not to include them into formulation approach for parenteral use, but to ascertain the potential solubility parameter requirements to solubilize the API.

This work evaluated the use of povidone for two (2) purposes to solve for the solubility issue and potential impact to stability for oxidative pathways as it is published in BASF Kollidon technical guide to use for such purposes. Structural analysis of lenalidomide and povidone and Pharmasolve likely tell the unique relationship between the API and the excipients, such that, the heart of the molecule of lenalidomide is similar in structure to Povidone and Pharmasolve, as shown in structures I, II, and III below.

Lenalidomide

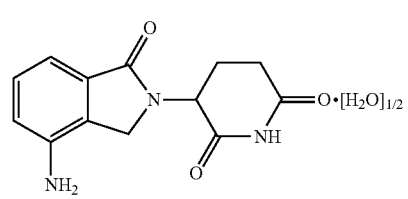

(Structure I)

Povidone

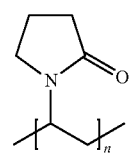

(Structure II)

Pharmasolve (n-methyl-2-pyrrolidone)

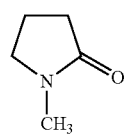

(Structure III)

LLD is soluble in NMP to approximately 30% by weight (~300 mg/mL) and aqueous povidone solvent improves aqueous solubility by approximately 2-3-fold in which the pyrrolidone basic structure is within each molecule allows for associations to be made with active drug substance, lenalidomide. Povidone improves solubility from about 0.2 mg/mL up to about 0.8 mg/mL. Further, the polymer chain of povidone has specific hydrogen bonding affinity which provides enhanced solubility and protection of the primary amine of lenalidomide, which is most susceptible to oxidation.

In some embodiments, for ES #3, LLD is added first and then NMP is added second until dissolution occurs. Dissolution is usually complete within approximately 15 minutes for volumes of approximately 20 mL. It should be appreciated, however, that larger scale production may require longer dissolution times. Also, without wishing to be bound by theory, it has been observed that the saturation point of LLD in NMP is approximately 30% such that the targeted 1.3% w/w range for ES #3 is still well below saturation point.

TABLE 4

LLD-SC-Entry Solutions (ES)

| Ingredients | ES #1 (mg/mL(%)) | ES #2 (mg/mL(%)) | ES #3 (mg/mL(%)) |
|---|---|---|---|
| Lenalidomide (LLD) | 2.5 (0.25%) | 2.5 (0.25%) | 13.0 (1.3%) |
| Kollidon K-12 (PVP) | 100.0 (10.00%) | 100.0 (10.00%) | — |
| n-methyl-2-pyrrolidone Pharmasolve (NMP) | 877.5 (87.75%) | 897.5 (89.75%) | 987.0 (98.7%) |
| Citric Acid Monohydrate | 20.0 (2.00%) | — | — |

TABLE 5

LLD-SC-Diluent Solutions (DS)

| Ingredients | DS #1 (mg/mL (%)) | DS #2 (mg/mL (%)) | DS #3 (mg/mL (%)) |
|---|---|---|---|
| Sodium Chloride (NaCl) | 4.5 (0.45%)* | 4.5 (0.45%)* | 3.0 (0.30%)* |
| Sodium Bicarbonate (NaHCO3) | 3.8 (0.38%) | 3.5 (0.35%) | 3.5 (0.35%) |
| Citric Acid Monohydrate | — | 4.7 (0.47%) | 4.7 (0.47%) |
| Kollidon K12 (PVP) | 75.0 (7.50%) | 75.0 (7.50%) | 75.0 (7.50%) |
| n-methyl-2-pyrrolidone Pharmasolve (NMP) | — | — | — |
| Water for Injection | 916.7 (91.67%) | 912.3 (91.23%) | 913.8 (91.38%) |

*NaCl is provided for isotonicity adjustment and may be decreased or increased as needed.

TABLE 6

LLD-SC - Finished Drug Product (FDP)-Final Dilutions/Concentrations

| Ingredients | ES #1:DS #1 (mg/mL(%)) | ES #2:DS #2 (mg/mL(%)) | ES #3:DS #3 (mg/mL(%)) |
|---|---|---|---|
| Dilution Schema | 1 mL:4 mL (5 mL total) | 1 mL:4 mL (5 mL total) | 1 mL:25 mL (26 mL total) |
| Lenalidomide (LLD) | 0.5 (0.05%) | 0.5 (0.05%) | 0.5 (0.05%) |
| Kollidon K-12 (PVP) | 80.0 (8.00%) | 80.0 (8.00%) | 72.1 (7.21%) |
| n-methyl-2-pyrrolidone Pharmasolve (NMP) | 175.5 (17.55%) | 179.5 (17.95%) | 37.96 (3.80%) |
| Sodium Chloride (NaCl) | 3.6 (0.36%) | 3.6 (0.36%) | 2.9 (0.29%) |
| Sodium Bicarbonate (NaHCO3) | 3.0 (0.30%) | 3.0 (0.30%) | 3.4 (0.34%) |
| Citric Acid Monohydrate | 4.0 (0.40%) | 3.8 (0.38%) | 4.5 (0.45%) |
| Water for Injection | 733.4 (73.34%) qs | 729.8 (72.98%) qs | 878.7 (87.87%) qs |

TABLE 7

LLD-SC-Entry Solutions (ES) Current Technology

| Ingredients | ES #4 (mg/mL(%)) | ES #5 (mg/mL(%)) | ES #6 (mg/mL (%)) |
|---|---|---|---|
| Lenalidomide (LLD) | 6.5 (0.65%) | 13.0 (1.30%) | 19.5 (1.95%) |
| n-methyl-2-pyrrolidone Pharmasolve (NMP) | 993.5 (99.35%) | 987.0 (98.70%) | 980.5 (98.05%) |

TABLE 8

LLD-SC-Diluent Solution (DS)-Current Technology

| Ingredients | DS #4 (mg/mL (%)) |
|---|---|
| Sodium Bicarbonate (NaHCO3) | 3.5 (0.35%) |
| Citric Acid Monohydrate | 4.7 (0.47%) |
| Kollidon K12 (PVP) | 75.0 (7.50%) |
| Water for Injection | 912.3 (91.23%) qs |

*NaCl is provided for isotonicity adjustment and may be decreased or increased as needed.

TABLE 9

LLD-SC-Finished Drug Product (FDP)-Final Dilutions/Concentrations

| Ingredients | ES #4:DS #4 (mg/mL(%)) | ES #5:DS #4 (mg/mL(%)) | ES #6:DS #4 (mg/mL(%)) |
|---|---|---|---|
| Dilution Schema | 0.4 mL to 10 mL* (10.4 mL total) | 0.4 mL to 10 mL* (10.4 mL total) | 0.4 mL to 10 mL* (10.4 mL total) |
| Lenalidomide (LLD) | 0.25 (0.025%) | 0.5 (0.050%) | 0.75 (0.075%) |

TABLE 9-continued

LLD-SC-Finished Drug Product (FDP)-Final Dilutions/Concentrations

| Ingredients | ES #4:DS #4 (mg/mL(%)) | ES #5:DS #4 (mg/mL(%)) | ES #6:DS #4 (mg/mL(%)) |
|---|---|---|---|
| Kollidon K-12 (PVP) | 72.1 (7.21%) | 72.1 (7.21%) | 72.1 (7.21%) |
| n-methyl-2-pyrrolidone Pharmasolve (NMP) | 38.21 (3.82%) | 37.96 (3.80%) | 37.71 (3.77%) |
| Sodium Bicarbonate (NaHCO$_3$) | 3.4 (0.34%) | 3.4 (0.34%) | 3.4 (0.34%) |
| Citric Acid Monohydrate | 4.5 (0.45%) | 4.5 (0.45%) | 4.5 (0.45%) |
| Water for Injection | 733.4 (73.34%) qs | 729.8 (72.98%) qs | 878.7 (87.87%) qs |

*Ratio of Entry Solution (ES) to Diluent Solution (DS) is 1:25 prepared as 1 part ES to 25 parts DS, with the Final Dilution Drug Product including 26 parts In some embodiments, the order of addition of components to produce particular DS formulations is not defined. Also, it should be appreciated that amounts of particular components, such as NaCl, may be adjusted for osmolality, for example after analysis on a VP osmometer. In some embodiments, an osmolality of approximately 300 mOs/kg to 600 mOs/kg is desirable for certain finished drug products.

In some embodiments, solutions of the present technology may include a polar aprotic solvent or polymer such as, but not limited to, n-methyl pyrrolidone (NMP), dimethyl sulfoxide (DMSO), dimethylformamide (DMF), dimethylacetamide (DMAc), polyvinyl caprolactam, povidone and copolymers thereof, and other polymers without functionality, however, may contain a similar structure comprising a polar aprotic nature or may be soluble in polar aprotic solvents without presenting a polar protic group (—OH). Additionally, certain embodiments may comprise Kollidon VA64 (a copolymer of PVP and vinyl acetate).

In some embodiments, the stable LLD solution, and formulations thereof, comprise a dose that is between 10% to 100% of the daily dose of a standard of care treatment, such as between 10-900%, 10-80%, 10-70%, 10%-60%, 10-50% or 10%, 11%, 12%, 13%, 14%, 15%, 16%, 17%, 18%, 19%, 20%, 21%, 22%, 23%, 24%, 25%, 26%, 27%, 28%, 29%, 30%, 40%, 41%, 42%, 43%, 44%, 45%, 46%, 47%, 48%, 49%, 50%, 60%, 61%, 62%, 63%, 64%, 65%, 66%, 67%, 68%, 69%, 70% to 80%, 80% to 90%, 90% to 100%, or 100% of the daily dose of a standard of care LLD treatment. In some embodiments, the standard of care treatment is intraperitoneal injection of, for example, 500 mcg of LLD once daily. In some embodiments, the standard of care treatment is FDA-approved once daily oral dose of about 2.5 mg, about 5 mg, about 10 mg, about 15 mg, about 20 mg, or about 25 mg of LLD per day, as Revlimid®.

In various embodiments, the stable LLD solutions, and formulations thereof, provided herein may be used to treat multiple myeloma, transfusion-dependent anemia due to low- or intermediate-1-risk myelodysplastic syndromes, mantle cell lymphoma, solid tumor cancers, and hematological cancers. The stable LLD solution may be mixed with a pharmaceutically acceptable carrier or combination of carriers for parenteral delivery.

Some formulations of the stable solution of LLD, as provided herein, comprise the stable LLD solution and a pharmaceutically acceptable carrier. The pharmaceutically acceptable carrier should be compatible with other ingredients of the stable LLD solution, if any, and not be harmful for the subject's health. Exemplary carriers for formulations include, without limitation, water, carboxymethyl cellulose (CMC), Tween 80, dimethyl sulfoxide (DMSO), ethanol, 2-hydroxypropyl-β-cyclodextrin, dextrose, and polyethylene glycol or copolymers thereof, such as PEG200, PEG 300, PEG400, PEG600, PEG800, PEG 1450, and or others.

In some stable LLD solutions, and formulations thereof, as provided herein, LLD is present at a concentration of between about 0.01 mg/mL to about 300 mg/mL (about 0.001 wt. % to about 30 wt. %), about 0.05 mg/mL to about 100 mg/mL (about 0.005 wt. % to about 10 wt. %), about 0.05 mg/mL to about 50 mg/mL (about 0.005 wt. % to about 5 wt. %), about 0.1 mg/mL to about 40 mg/mL (about 0.01 wt. % to about 4 wt. %), about 0.1 mg/mL to about 25 mg/mL (about 0.01 wt. % to about 2.5 wt. %), or between about 0.2 mg/L and about 10 mg/mL (about 0.02 wt. % and about 1 wt. %). In other embodiments, the stable solution formulation of LLD comprises between about 0.1 mg/mL and about 20.0 mg/mL LLD (about 0.01 wt. % and about 2 wt. %). For example, in some embodiments the stable formulation of LLD comprises about 0.1 mg/mL, about 0.25 mg/mL, about 0.5 mg/mL, about 0.75 mg/mL, about 1.0 mg/mL, about 2.0 mg/mL, about 2.5 mg/mL, about 3.0 mg/mL, about 4.0 mg/mL, about 6.0 mg/mL, about 8.0 mg/mL, about 10.0 mg/mL, 12.0 mg/mL, about 14.0 mg/mL, about 15.0 mg/mL, or about 20 mg/mL LLD (about 0.01 wt. %, about 0.025 wt. %, about 0.05 wt. %, about 0.075 wt. %, about 0.1 wt. %, about 0.2 wt. %, about 0.25 wt. %, about 0.3 wt. %, about 0.4 wt. %, about 0.6 wt. %, about 0.8 wt. %, about 1 wt. %, about 1.2 wt. %, about 1.4 wt. %, about 1.5 wt. % or about 2 wt. %) in the final composition for administration.

According to the present disclosure, the inventors have unexpectedly found that certain solutions comprising LLD and additional components provide a solution with increased LLD solubility and superior LLD stability. For example, certain LLD solutions provided herein provide mitigation of both hydrolysis and oxidative degradation of LLD by incorporation of both polar aprotic solvent and povidone at physiological pH.

In some embodiments, the stable LLD solutions, and formulations thereof, provided herein further comprise a polymer, such as a water-soluble polymer. In some embodiments, the stable LLD solutions, and formulations thereof, include polyvinylpyrrolidone (PVP), also commonly called polyvidone or povidone. PVP is a water-soluble polymer made from the monomer N-vinylpyrrolidone. In some embodiments, PVP is present in entry solutions, diluent solutions, and/or final diluted LLD formulations of the present technology. In other embodiments, PVP is present in both entry and diluent solutions of the present technology.

In some embodiments, the stable LLD solutions, and formulations thereof, provided herein further comprise PVP having a molecular weight of about 2 k to about 70 k (wherein k represents an average molecular weight (K-value) which is calculated based on the relative viscosity of the polymer in water).

In yet further embodiments, the stable LLD solutions, and formulations thereof, described herein allow for reduced variability in dosage of the active components in a patient over a predetermined time. In some embodiments, the predetermined time period is up to 24 hours, 48 hours, 72 hours, 96 hours, 120 hours, 144 hours, 7 days, 8 to 13 days, two weeks, 15 days, 21 days, 28 days, in cycles of or for longer.

In embodiments, the stable LLD solution, and formulations thereof, may comprise one or more optional carriers and excipients, some of which may have dual or multiple functionalities, e.g., a particular excipient may function as, e.g., a solubilizer or stabilizer. Optional carriers or excipients include, without limitation, solvents, solubilizers, diluents, suspending agents, dispersing agents, gelling agents, polymers, biodegradable polymers, penetration enhancers, plasticizers, pH-adjusting agents, buffering agents, pH stabilizers, emulsifying agents, auxiliary emulsifying agents, surfactants, suspending agents, stabilizers, preservatives, chelating agents, complexing agents, emollients, humectants, demulcents, skin irritation reducing agents, antioxidants, oxidants, tackifiers, fillers, and volatile chemicals.

In embodiments, the stable LLD solution, and formulations thereof, may comprise a solvent, e.g., one or more of a C1-C20 alcohol (e.g., without limitation, one or more of: methanol, ethanol, isopropyl alcohol, butanol, propanol, 2-methyl-2-propanol, aka t-butyl alcohol, pentanol, 2,4-dimethyl-2-pentanol, 3,5-dimethyl-3-hexanol, and alcohols having C7, C8, C9, C10, C11, C12, C13, C14, C15, C16, C17, C18, C19 or C20 carbon atoms), polyhydric alcohols, glycols (e.g., without limitation: propylene glycol, polyethylene glycol, dipropylene glycol, hexylene glycol, butyene glycol, glycerine), derivatives of glycols, pyrrolidone (e.g., without limitation: N-methyl 2-pyrrolidone, 2-pyrrolidone), sulfoxides (e.g., without limitation: dimethyl sulfoxide (DMSO)), dimethyl isosorbide, mineral oils, vegetable oils, water, polar solvents, semi polar solvents, non-polar solvents, esters, ketones, alcohols, alkanes, such as ethyl acetate, acetone, dichloromethane, chloroform, heptane, hexane, siloxanes, ethanol, isopropanol, toluene, and acids such as acetic acid, lactic acid, levulinic acid, and bases.

In embodiments, the stable LLD solution, and formulations thereof, may comprise a surfactant, solubilizer, emulsifying agent, or dispersing agent, including anionic, cationic, nonionic and amphoteric surfactants, e.g. one or more of a propylene glycol, monocaprylate type I, propylene glycol monocaprylate type II, propylene glycol dicaprylate, medium chain triglycerides, propylene glycol monolaurate type II, linoleoyl polyoxyl-6 glycerides, oleoyl-polyoxyl-6-glycerides, lauroyl polyoxyl-6-gylcerides, polyglyceryl-3-dioleate, diethylene glycol monoethyl ether, propylene glycol monolaurate type I, polyglyceryl-3-dioleate, caprylocaproyl polyoxyl—8 glycerides, cyclodextrins, Diethylene glycol monoethyl ether (DEGEE), a polysorbate/polyethoxylated sorbitan ester or Tween®-type surfactant, a sorbitan ester or Span®-type solvent surfactant, a glycol, hexylengycol, a Brij® type surfactant, and sodium lauryl sulfate. DEGEE (also known as Di(ethylene glycol) ethyl ether or 2-(2-Ethoxyethoxy)ethanol)) is commercially available e.g., under the various trade names including Transcutol® (TC), Transcutol® P, Transcutol® CG, Transcutol® HP (Gattefosse, Lyon, France), and Carbitol™ (Dow Chemicals, Midland MI). The Span® or Tween® surfactant may, without limitation, be selected from one or more of: Span 20®, Span®40, Span®60, Span®80, Span®83, Span®85, Span®120, Tween 20®, Tween 21®, Tween 40®, Tween 60®, Tween 61®, Tween 65®, and Tween 80®. Brij® is a group of nonionic surfactants commercially available from various sources (e.g. Sigma-Aldrich), and may be selected from one or more of Brij® 93 (average Mn~357), Brij® S 100 (average Mn 4,670), Brij® 58 (average Mn 1124), Brij® 010 (average Mn~709, also known as Brij 97, (Polyoxyethylene (10) oleyl ether), Brij® C10 (average Mn~683), Brij® L4 (average Mn~362, also known as polyethylene glycol dodecyl ether, polyoxyethylene (4) lauryl ether), BRIJ® 020 (average Mn 1,150, (Polyoxyethylene (20) oleyl ether), Brij® S2 MBAL (also known as Brij® S2, polyethylene glycol octadecyl ether, polyoxyethylene (2) stearyl ether, (diethylene glycol octadecyl ether), Brij® S10 (average Mn~711), Brij® S20, and Brij® 35 (also known as Brij® L23(polyoxyethylene lauryl ether). Suitable amounts of a surfactant to include into formulations to perform a surfactant function may be from 0.01 wt. % to about 95 wt. %. In some embodiments, the surfactant maybe present at a concentration of less than about 5% wt. %, such as less than about 4 wt. %, less than about 3 wt. %, less than about 2 wt. %, less than about 1 wt. %, or less than about 0.5 wt. %. Suitable amounts for solvent/solubilizing functions may be present in the formulation at a concentration ranging from about 5 wt. % to about 50 wt. %. Amounts may be increased or decreased to achieve a suitable and sufficient amount, as will be apparent to a person of ordinary skill in the art.

A glycol is class of small organic compounds (e.g., MW typically below 150 Daltons), or a polymer thereof, that belongs to the alcohol family, and wherein two hydroxyl (—OH) groups are attached to different carbon atoms. The simplest member of the glycol class is ethylene glycol (also known as 1,2-ethanediol), other members include, without limitation, propylene glycol (also called 1,2-propanediol), butylene glycol (1,3-butanediol), 1,4-butanediol, pentylene glycol, (1,2-pentanediol), hexylene glycol (2,4-pentanediol), 2-ethyl-1,3-hexanediol, and 2-methyl-2-propyl-1,3-propanediol. Similarly, higher molecular weight polymers of the above glycol diols, in particular of ethylene glycol, may be used; these include, without limitation, polyethylene glycol (PEG). PEGs are available in different molecular weights, typically from about 200 g/mol to about 10,000,000 g/mol, e.g., PEG 200, 300, 400, 600, 800, 1000, 1500, 3350, 4000, 6000, 8000, 10,000, 20,000, 35,000. PEGs of different molecular weight have similar surfactant properties but the higher molecular weight polymers may be preferred.

Further optional excipients include for example, without limitation, one or more pH adjusting and buffering agents selected from, without limitation, buffers (e.g. citrate buffer, phosphate buffer, acetate buffer), acids and acid derivatives (e.g. carboxylic acid, organic acid, inorganic acid, sulfonic acid, halogenated carboxylic acids, vinylogous carboxylic acids, hydrochloric acid, acetic acid, succinic acid, citric acid, ascorbic acid, phosphoric acid), bases and base derivatives, e.g. sodium bicarbonate, sodium carbonate, trimethylamine, triethanolamine, sodium hydroxide, calcium hydroxide, potassium hydroxide, ammonium hydroxide, and tromethamine. Preferably, weak organic acids or weak organic bases are used as pH adjusting agents. The pH adjusting/buffering agent or stabilizer helps to maintain the appropriate pH of the formulation.

Still further optional excipients include for example, without limitation, one or more of cyclodextrins and derivatives thereof, amino acids, emulsifying agents, auxiliary emulsifying agents, surfactants, suspending agents, preservatives, antioxidants, chelating agents, emollients, humectants, demulcents, skin irritation reducing agents, tackifiers, fillers, cross-linking agents, resins, crystallization inhibitors, and clays.

Such optional emulsifying agents, auxiliary emulsifying agents, surfactants and suspending agents may include, without limitation, one or more of monoglycerides, diglycerides, polyoxyl stearate, a mixture of triceteareth-4 phosphate with ethylene glycol palmitostearate and with diethylene glycol palmitostearate, polyglyceryl-3 diisostearate, a mixture of PEG-6 stearate with ethylene glycol palmitostearate and with PEG-32 stearate, oleoylpolyoxyl-6 glycerides, lauroyl polyoxyl-6 glycerides, caprylocaproyl polyoxyl-8 glycerides, propylene glycol monocaprylate type I, propylene glycol monolaurate type II, propylene glycol monolaurate type I, propylene glycol monocaprylate type II, polyglyceryl-3 dioleate, a mixture of PEG-6 stearate with PEG-32 stearate, lecithin, cetyl alcohol, cholesterol, bentonite, veegum, magnesium hydroxide, dioctyl sodium sulfosuccinate, sodium lauryl sulfate, triethanolamine stearate, potassium laurate, polyoxyethylene fatty alcohol ethers, glyceryl monostearate, polyoxyethylene poloxypropylene block copolymers (poloxamers), sorbitan monolaurate, lanolin alcohols and ethoxylated lanolin alcohols, sorbitan fatty acid esters, sucrose distearate, sodium alginate, alginic acid, hectorite, aluminum silicate, polysorbate (e.g. polysorbate 20, polysorbate 40, polysorbate 60, polysorbate 80 etc.), and Span® surfactant products (e.g., Span® 80, Span® 20).

Additional preservatives and stabilizers may be selected from, without limitation, one or more of sodium metabisulfite, citric acid, ascorbic acid, vitamin E, butylated hydroxyanisole (BHA), butylated hydroxytoluene (BHT), alpha tocopherol, ascorbyl palmitate, propionic acid, sodium bisulfate, propyl gallate, gallic acid, monothioglycerol, sodium ascorbate, benzethonium chloride, chlorhexidine, phenylethyl alcohol, chloroxylenol, cresol, hexetidine, phenoxyethanol, chlorobutanol, ascorbic acid, benzoic acid, sodium benzoate, sorbic acid, potassium sorbate, potassium metabisulfite, phenol, potassium benzoate, dehydroacetic acid, cetylpyridinium chloride, methylparaben, propylparaben, butylparaben, benzyl alcohol, benzalkonium chloride, and discoloring agents.

Chelating agents may be selected from, without limitation, one or more of sodium edetate, edetic acid, tartaric acid, fumaric acid, disodium edetate, trisodium edetate, dipotassium edetate).

Fillers may be selected from, without limitation, one or more of lactose, magnesium stearate, mannitol, starch, sugars, titanium dioxide, talc, shellac, colloidal silicone dioxide, kaolin, magnesium oxide, clays.

Degradation Analyses

Formulations of LLD were analyzed for providing protection from degradation, such as forced oxidative and hydrolytic degradation. Various formulations of drugs, such as LLD drugs, in solution were evaluated in the presence of reagents and solvents necessary to understand the stability of API to determine potency and purity of the primary peak of reference. The primary analytical method for analysis of drug substance in solution is a stability-indicating method, which identifies and quantitates various primary and degradative peaks of the API by HPLC. For example, formulations comprising LLD can be analysis for the LLD primary peak of interest and the assessment for known and unknown impurities. In the case of LLD, there are no less than two (2) peaks of interest through hydrolysis and no less than two (4) peaks of interest through oxidation pathways.

In the process of the analytical evaluation, forced degradation of the API in solution is performed to assess how identified chromatography peaks, primary and degradation/impurity are formed. Forced degradation of analytical solutions and standards exhibit significant degradation by various hydrolytic and oxidative pathways. As shown in FIGS. 1-4, the HPLC chromatograms of LLD solutions when exposed to acidic, basic, or oxidative conditions under thermal stress (40° C.) exhibit various patterns of primary and degradative peaks.

Figure 2:
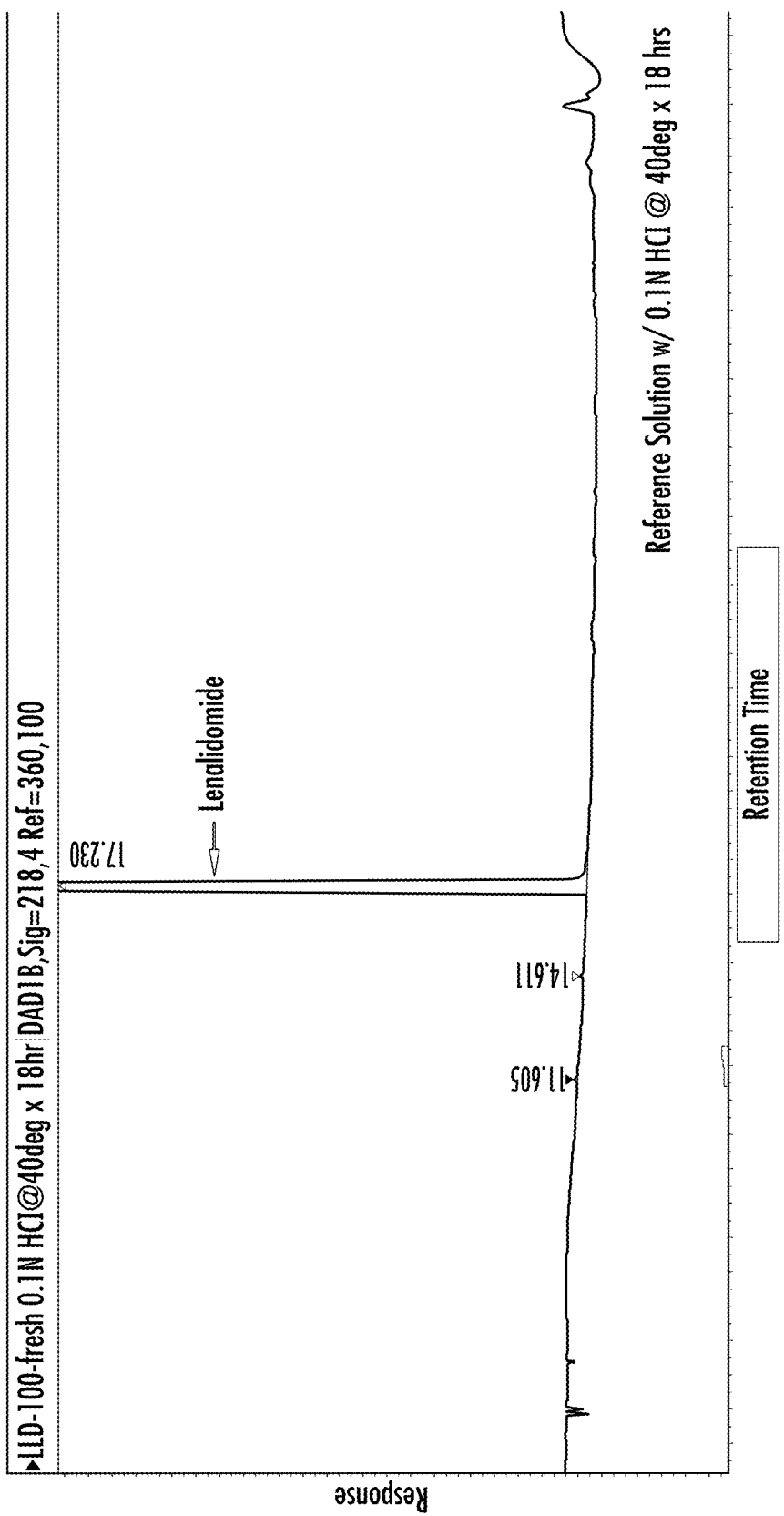
FIG. 2 is an HPLC chromatogram of an LLD sample stored under acidic conditions.
Figure 3:
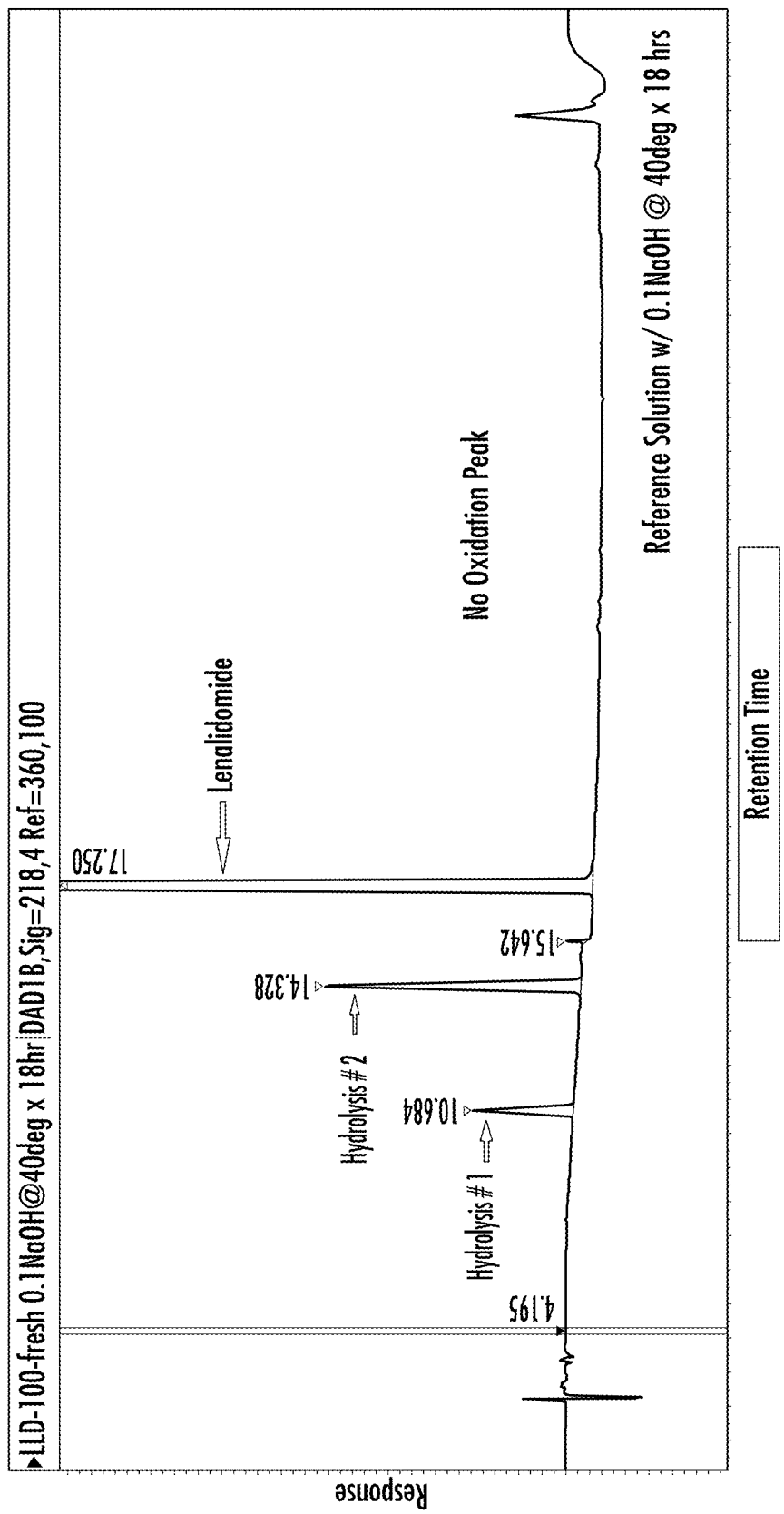
FIG. 3 is an HPLC chromatogram of an LLD sample stored in a sodium hydroxide solution to force hydrolytic degradation.
Figure 4:
FIG. 4 is an HPLC chromatogram of an LLD sample stored in a peroxide solution to force oxidative degradation.

Specifically, for LLD, no apparent degradation events were detected in the reference standard solution held at ambient temperature (FIG. 1). It was also found that LLD is relatively stable under acidic conditions with limited detection of hydrolysis or oxidation peaks (FIG. 2). However, under a forced degradation study with sodium hydroxide hydrolytic conditions, LLD is susceptible degradation into two (2) hydrolysis peaks as shown (FIG. 3). Also, under forced degradation studies with peroxide oxidative conditions, LLD is susceptible significant oxidation as shown (FIG. 4).

Additional LLD formulations were also analyzed to further ascertain the development of hydrolytic and oxidative degradation pathways of LLD by incorporation of both a polar protic solvent (Isopropyl Alcohol, IPA) or a polar aprotic solvent (Acetonitrile, ACN) in the presence of the LLD. Accordingly, the present technology provides analysis of potential additional degradation pathways for LLD where certain characteristics of a functional solvent (—OH) or an inert or non-functional solvent (ACN) can be studied. As shown in FIGS. 5-8, the present technology provides evaluation of forced degradation by peroxide oxidation and by basic hydrolysis of LLD in presence of IPA, a polar protic solvent, or ACN, a polar aprotic solvent.

Figure 5:
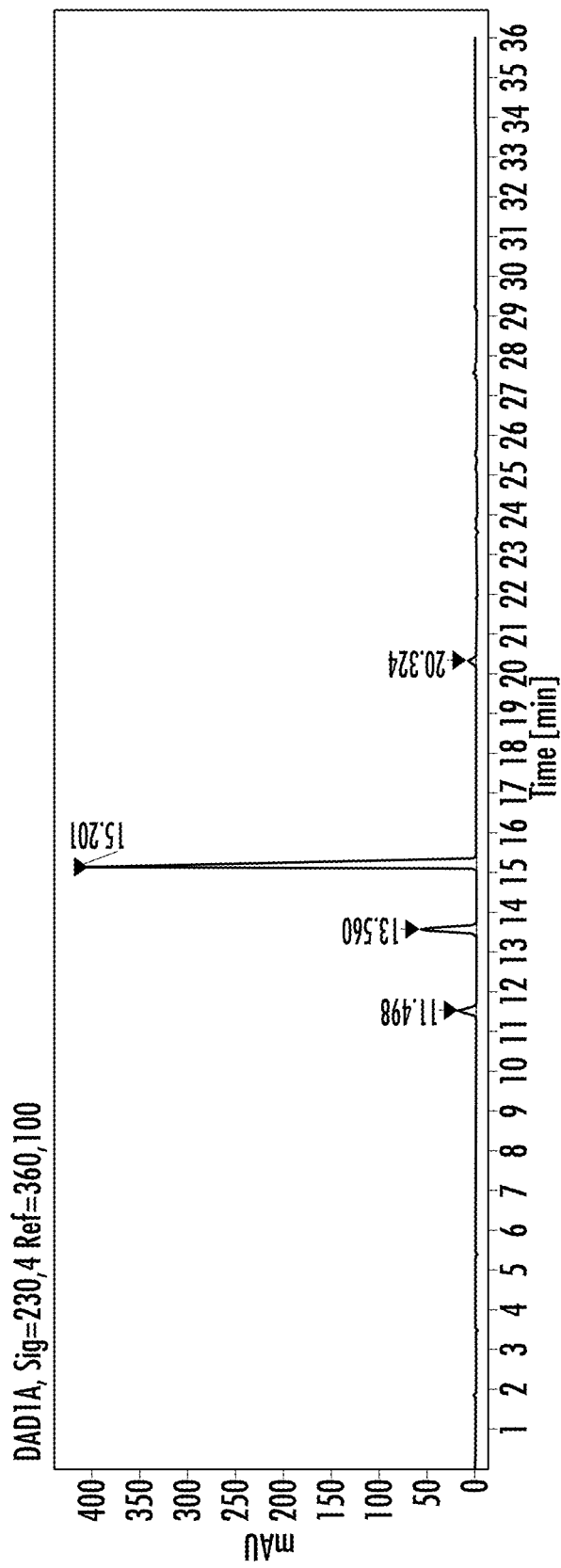
FIG. 5 is an HPLC chromatogram of an LLD sample stored in the presence of isopropyl alcohol under forced oxidative degradation conditions.
Figure 6:
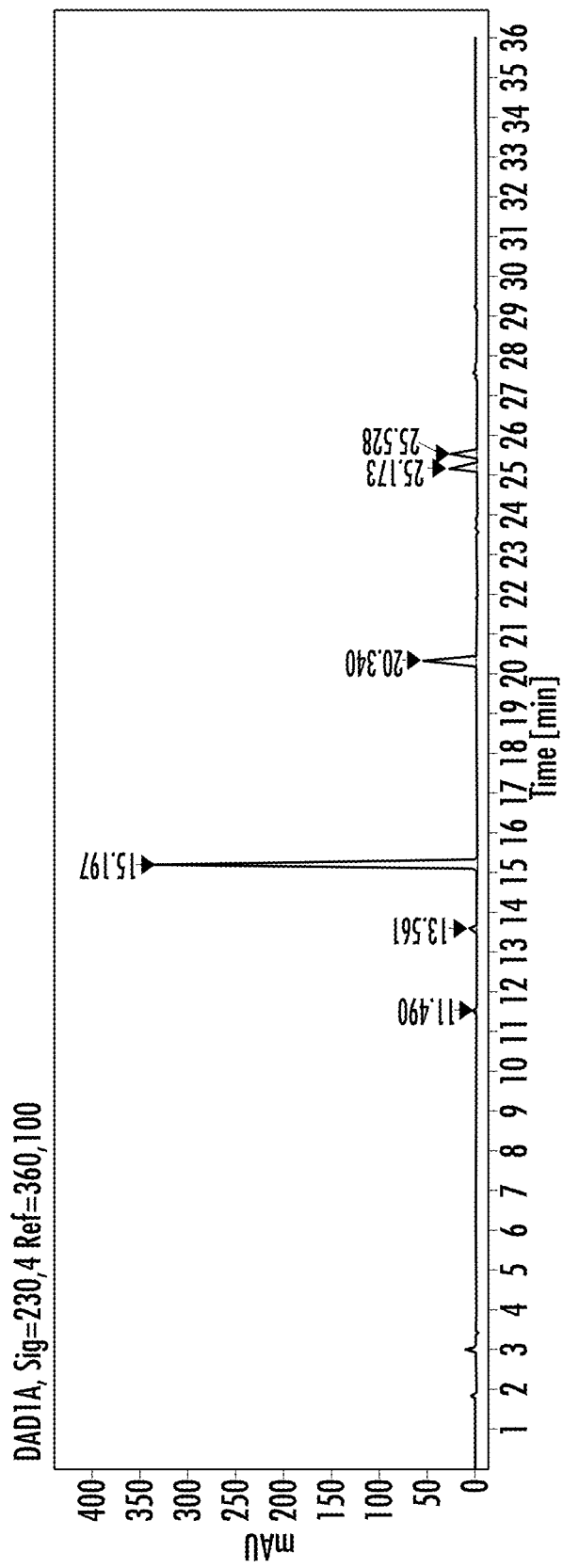
FIG. 6 is an HPLC chromatogram of an LLD sample stored in the presence of acetonitrile under forced oxidative degradation conditions.

In some embodiments, it was found that in presence of IPA forced degradation through oxidative pathway protected against some oxidation (RT 20.324), however, significant hydrolysis occurred (FIG. 5, RT 11.498 and RT 13.560). It was also found that, in the presence of ACN, forced degradation of LLD through oxidative pathways protected against some hydrolysis (FIG. 6, RT 11.490 and RT 13.561), however, significant oxidation occurred (FIG. 6, RT 20.340, RT 25.173, and RT 25.528).

Figure 7:
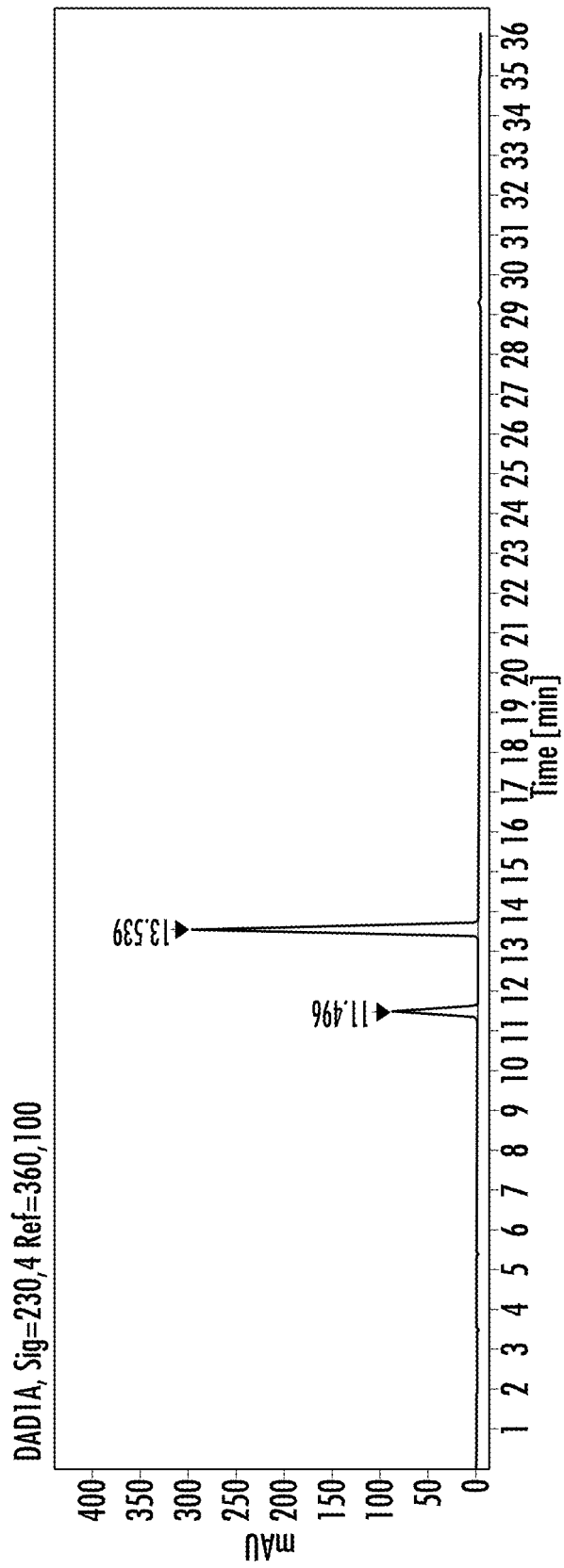
FIG. 7 is an HPLC chromatogram of an LLD sample stored in the presence of isopropyl alcohol under forced hydrolytic degradation conditions.
Figure 8:
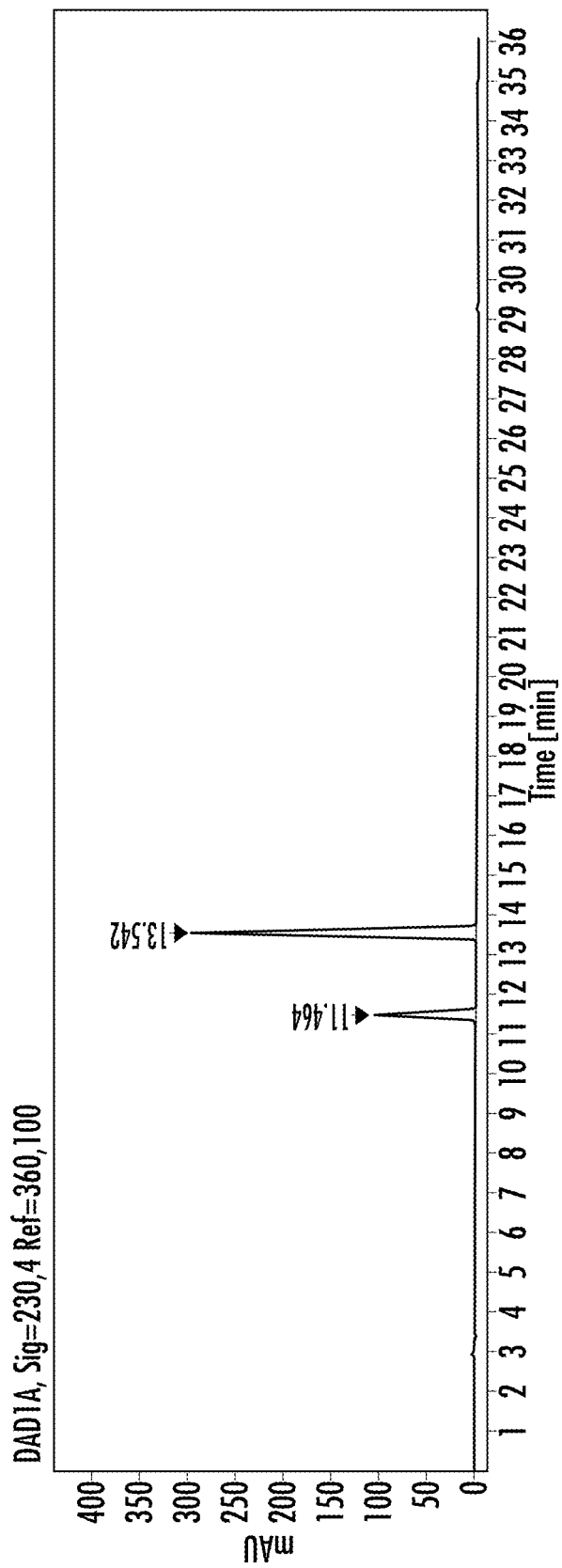
FIG. 8 is an HPLC chromatogram of an LLD sample stored in the presence of acetonitrile under forced hydrolytic degradation conditions.
Figure 9:
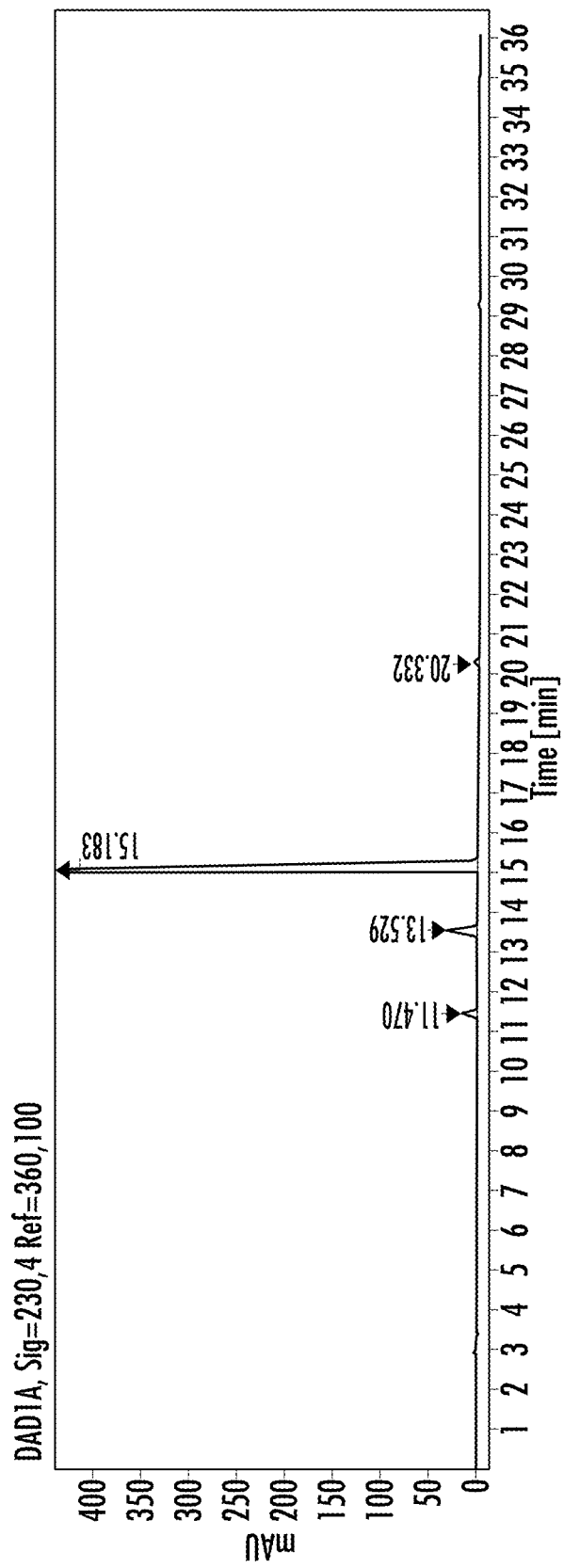
FIG. 9 is an HPLC chromatogram of an LLD sample stored in the presence of 1% PEG400 under forced hydroxide oxidative degradation conditions.
Figure 10:
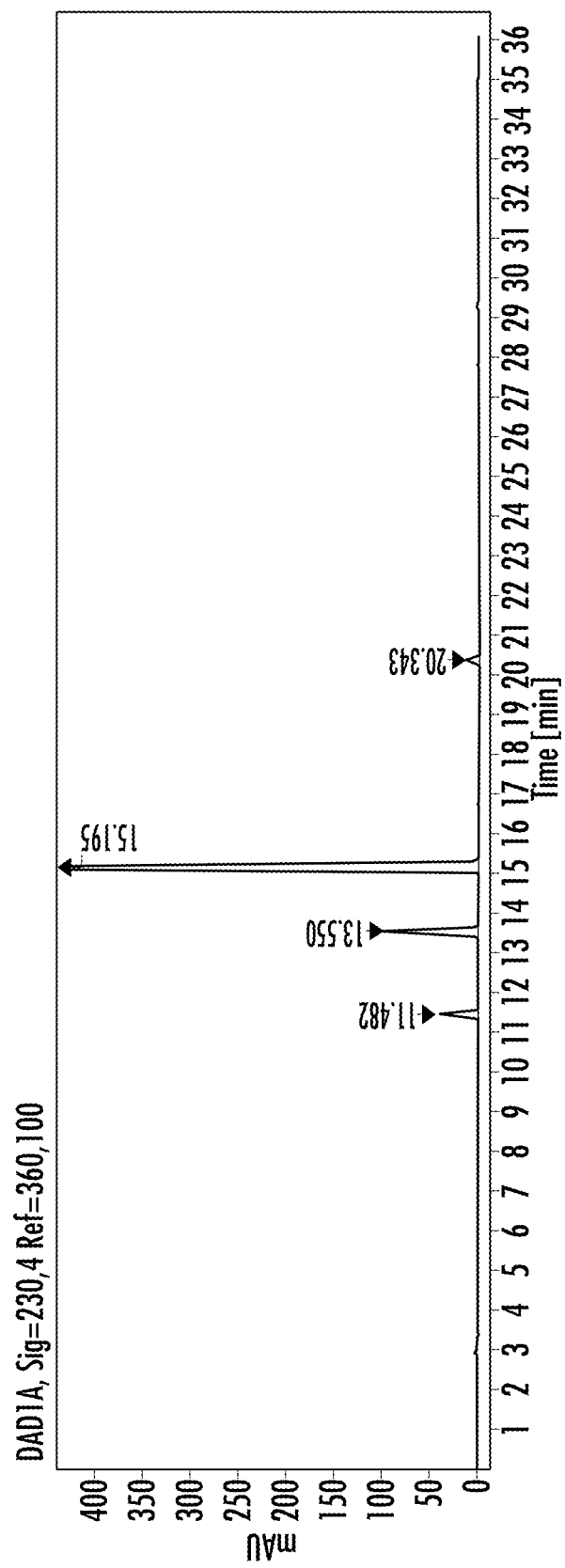
FIG. 10 is an HPLC chromatogram of an LLD sample stored in the presence of 1% PG under forced hydroxide oxidative degradation conditions.

In other embodiments, it was found that LLD in the presence of IPA forced degradation through basic hydrolysis pathway did not protect against any hydrolysis (FIG. 7, RT 11.496 and RT 13.539). There was 100% loss of LLD (FIG. 7, RT~15.2) and no oxidation observed (FIG. 7, RT~20.3). Moreover, certain embodiments demonstrate that the presence of ACN forced degradation through basic hydrolysis pathway did not protect against any hydrolysis (FIG. 8, RT 11.464 and RT 13.542). There was 100% loss of LLD (FIG. 8, RT~15.2) and no oxidation observed (FIG. 8, RT~20.3).

Accordingly, the present technology provides that LLD is protected from oxidation by polar protic solvents and protected from hydrolysis by polar aprotic solvents under oxidative stress conditions. However, in certain embodiments, neither IPA nor ACN could prevent hydrolysis under extreme basic conditions. Without being bound by any scientific theory, it is believed that when a polar protic solvent is used, any (—OH) alcohol group would pose significant issues with stability due to hydrolysis and that if a polar aprotic solvent is used it is suspected any polar aprotic solvent may pose stability concerns due to oxidation. Similar to antioxidants that are well-known and well-understood in pharmaceutical use, and more specifically in parenteral use, the use of a polar aprotic solvent or excipient which could function in a polar aprotic nature, such as PVP, and is suitable for parenteral use in pharmaceutical products would be considered a viable candidate to prevent the hydrolysis and an antioxidant could be evaluated to protect from oxidation.

In other embodiments, the current technology provides that the use of PVP in the presence of polar aprotic solvents, such as, n-methyl-2-pyrrolidone (NMP), has significant protection of LLD degradation. Other polar aprotic solvents that also provide such protections from degradation may also include DMSO, DMF, DMAc and ACN. In some embodiments, solutions of the present technology comprise NMP due to regulatory precedence in approved drug products by FDA. Where combinations of NMP and PVP (K-12) in ratios from about 99:1 to about 50:50, and preferably from about 98:2 to about 80:20, and where NMP, K-12 and LLD combinations without presence of water exhibits superior stability for long term storage and accelerated conditions, and where polar aprotic solvents in the presence of water, alone are not sufficient to protect the API from hydrolysis, however, in combination with PVP, >90% of hydrolytic degradation and nearly 100% of oxidation is mitigated in presence of water.

In some embodiments, the combination of NMP:Povidone:LLD, as a concentrate, is not suitable as a stand-alone drug product as it may expose the patient to levels of NMP or povidone outside of the accepted ranges according to the FDA IIG. However, the combination provides significant stability improvements for long-term storage at room temperature conditions for the drug product. According to certain embodiments of the present technology, a diluent would be added at time of administration to a patient to maintain stability for no less than the duration of administration. In accordance with other embodiments, certain combinations may show viability for long-term storage without diluent step.

In still other embodiments, acidic conditions increase stability of API, such as LLD, such that below pH 4.5, the API exhibits negligible total related impurities. However, less than pH 4.5 is not suitable for injection or for subcutaneous infusion. Thus, diluting certain embodiments of NMP:povidone concentrate with a specific combination of excipients allows production an isotonic solution with appropriate pH between about 5.0 to about 6.5.

In other embodiments, stable solutions of IMiDs, such as stable solutions of LLD, may comprise any one of many acids, such as Hydrochloric acid, Phosphoric acid, Acetic acid, ascorbic acid, adipic acid, benzoic acid, boric acid, EDTA, edetic acid, formic acid, fumaric acid, nitric acid, sorbic acid, succinic acid, sulfuric acid, tartaric acid, gallic acid, amino acids, and citric acid. In some embodiments, any acid which is soluble in NMP is viable for inclusion in the present solutions and would have the ability to provide suitable environment for drug solution. In some embodiments, citric acid monohydrate is included in the compositions of the present technology and has been found to be particularly soluble in NMP and PVP concentrate.

In other embodiments, the solutions of the present technology may comprise a neutralizing agent, such as sodium or potassium salts of citrates, chlorides, hydroxides, bicarbonates, carbonates, sulfonates and weak organic bases such as tris or triethanolamine have been found to be useful. In some embodiments, sodium bicarbonate was found to provide utility in diluent solution in combination with an isotonic concentration of sodium chloride in a final pH range of about 5.0 to 6.5 overall, and more preferably between about pH 5.5 to about pH 6.0.

Certain embodiments of the stable solutions of LLD of the present technology comprise povidone (PVP), a pharmaceutically acceptable polymer. Without wishing to be bound by theory, PVP is thought to provide an excipient which may function in a polar aprotic nature by structure, the polymer contains a 5-member ring with a tertiary amine and a ketone in a specific arrangement. Thereby, this type of polymer may avoid the use of an alcohol (—OH) group excipient, however, provides for a structure which is polar aprotic in nature.

Accordingly, some embodiments of the stable LLD solutions of the present technology comprise PVP K-12, with a molecular weight range of about 2,000 to about 3,000, and/or, PVP K-30 with a molecular weight range of about 44,000 to about 54,000. Also, without wishing to be bound by theory, different PVP molecular weight ranges are also thought to differences in solubility, viscosity and other aspects. The structures below provide the basic chemical structure of soluble grades of PVP as provided by BASF which would include grades K-12 through K-90.

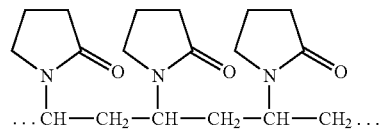

As shown in FIGS. 9-16, the present technology provides evaluation of forced degradation by peroxide oxidation and by basic hydrolysis of LLD in presence of various formulations comprising PVP and PEG and PG, as follows.

Solutions of LLD including 1% PEG400 were exposed to forced degradation by peroxide oxidation where hydrolysis (FIG. 9, RT 11.470 and RT 13.529) and oxidation (FIG. 9, RT 20.332) are both exhibited. Solutions of LLD including 1% PG were exposed to forced degradation by peroxide oxidation where hydrolysis (FIG. 10, RT 11.482 and RT 13.550) and oxidation (FIG. 10, RT 20.343) are both exhibited.

Figure 11:
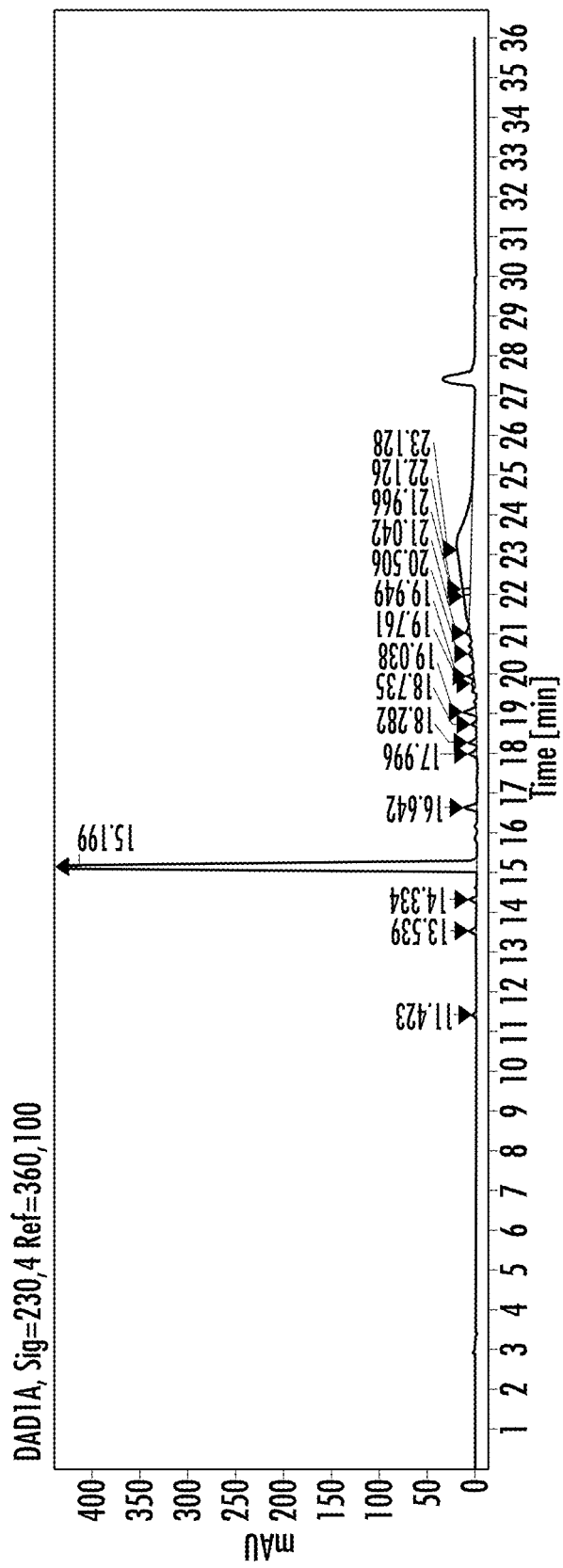
FIG. 11 is an HPLC chromatogram of an LLD sample stored in the presence of 1% PVP K-12 under forced hydroxide oxidative degradation conditions.
Figure 12:
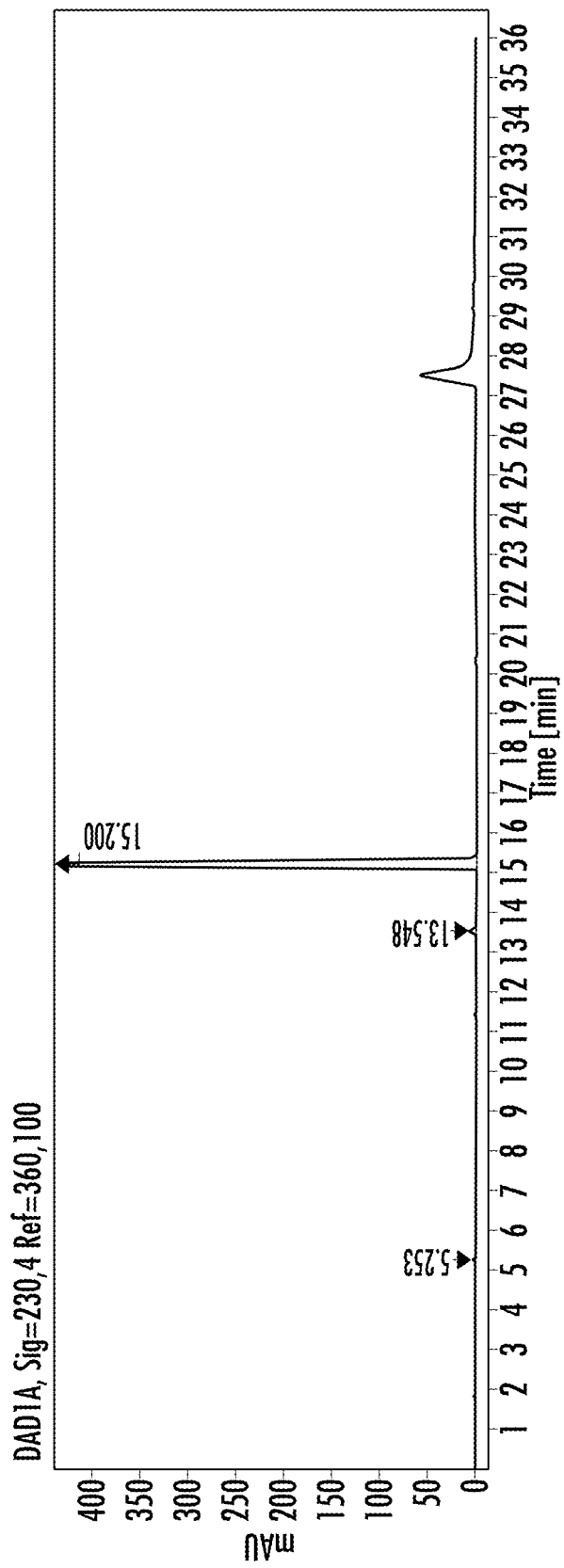
FIG. 12 is an HPLC chromatogram of an LLD sample stored in the presence of 1% PVP K-30 under forced hydroxide oxidative degradation conditions.

Solutions of LLD including 1% PVP K-12 were exposed to forced degradation by peroxide oxidation where very little hydrolysis occurs (FIG. 11, RT 11.423 and RT 13.539) and oxidation related substances are not present. Most if not all of the peaks observed after the LLD peak in FIG. 11 are placebo related to Kollidon K-12, and not related to LLD. Solutions of LLD including 1% PVP K-30 were exposed to forced degradation by peroxide oxidation where there is almost no hydrolysis observed (FIG. 12, RT 13.548) and no oxidation. The peak at RT 5.253 of FIG. 12 is placebo related to Kollidon 30.

Figure 13:
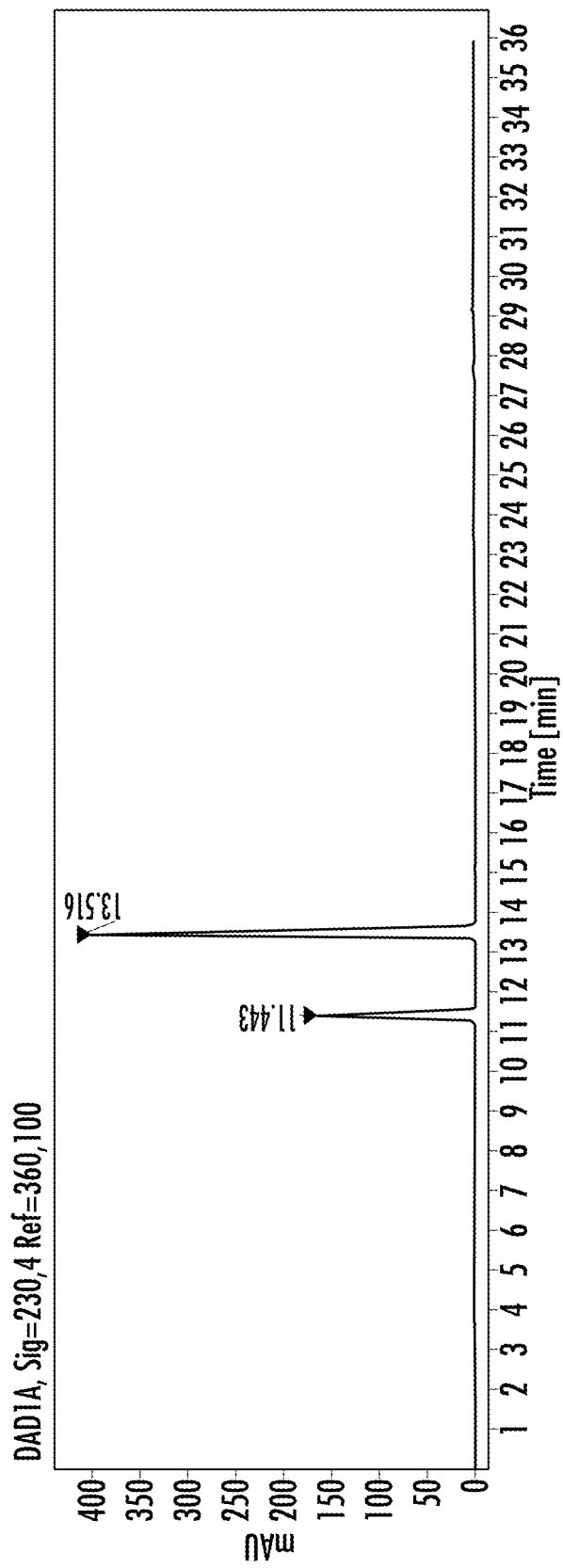
FIG. 13 is an HPLC chromatogram of an LLD sample stored in the presence of 1% PEG400 under forced basic hydrolytic degradation conditions.
Figure 14:
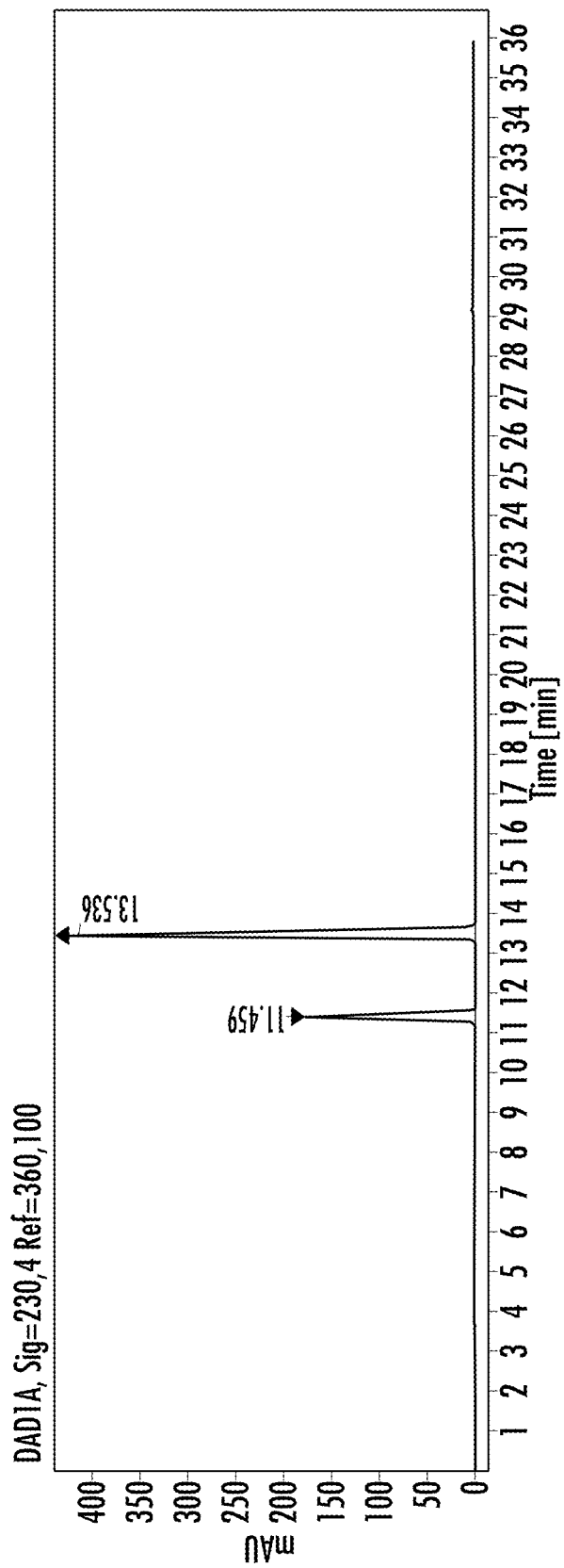
FIG. 14 is an HPLC chromatogram of an LLD sample stored in the presence of 1% PG under forced basic hydrolytic degradation conditions.

Solutions of LLD including 1% PEG400 were exposed to forced degradation by basic hydrolysis where significant hydrolysis is present (FIG. 13, RT 11.443 and RT 13.516) but no oxidation (FIG. 13, RT~20.3). However, 100% of the LLD (FIG. 13, RT~15.2) is degraded. Solutions of LLD including 1% PG were exposed to forced degradation by basic hydrolysis where significant hydrolysis is present (FIG. 14, RT 11.459 and RT 13.536) abut no oxidation (FIG. 14, RT~20.3). However, 100% of the LLD (FIG. 14, RT~15.2) is degraded.

Figure 15:
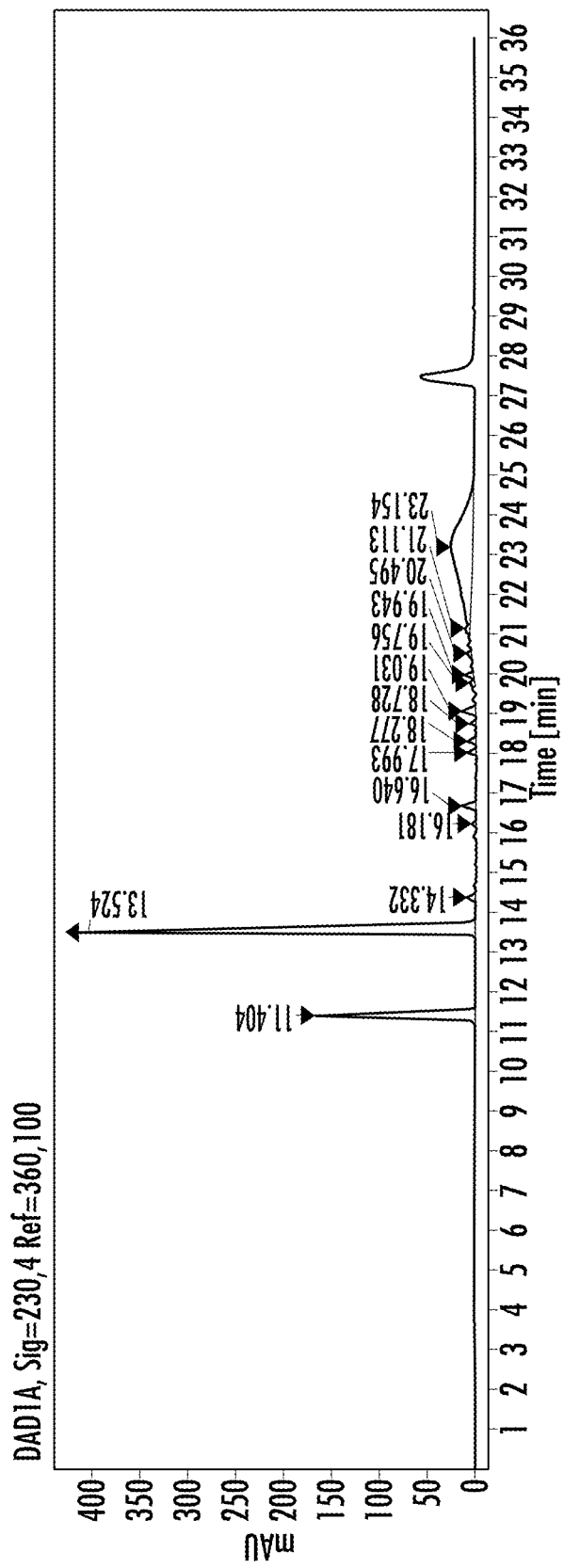
FIG. 15 is an HPLC chromatogram of an LLD sample stored in the presence of 1% PVP K-12 under forced basic hydrolytic degradation conditions.
Figure 16:
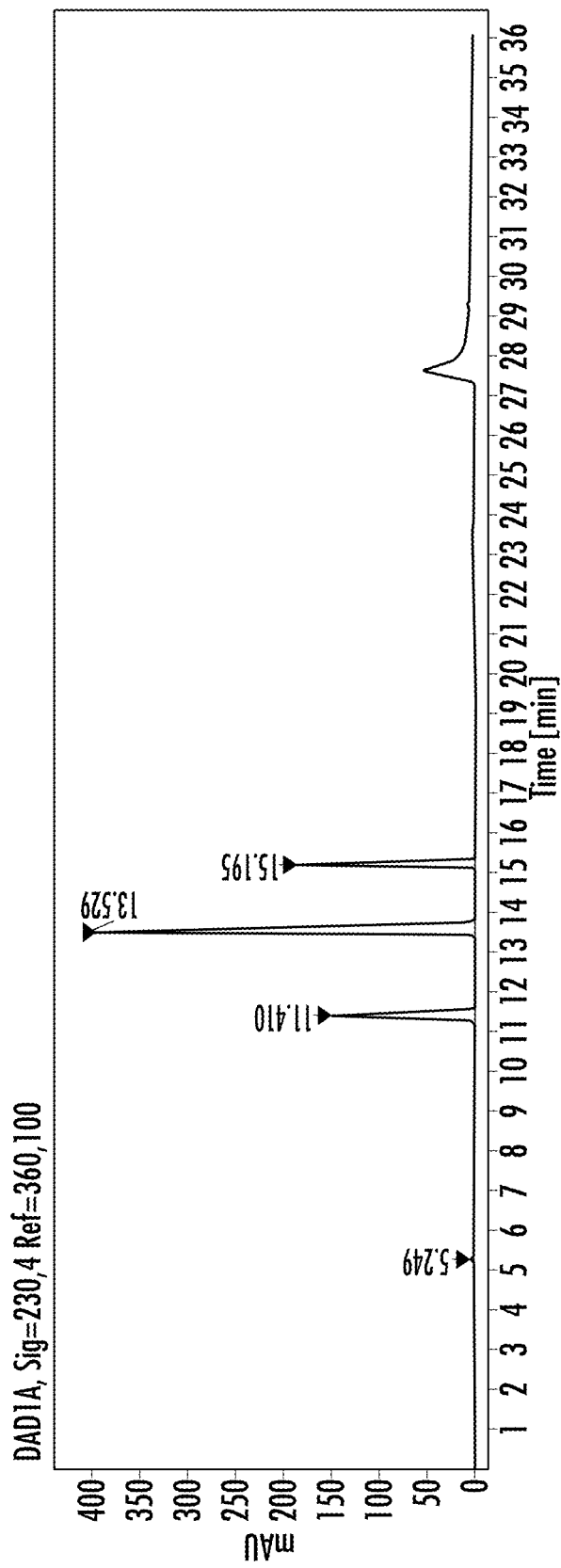
FIG. 16 is an HPLC chromatogram of an LLD sample stored in the presence of 1% PVP K-30 under forced basic hydrolytic degradation conditions.

Solutions of LLD including 1% PVP K-12 were exposed to forced degradation by basic hydrolysis where significant hydrolysis occurs (FIG. 15, RT 11.404 and RT 13.524) but no oxidative peaks. There was 100% degradation of LLD (FIG. 15, RT~15.2). As with FIG. 11 above, peaks after LLD RT~15.2 are placebo peaks related to Kollidon K-12.

Solutions of LLD including 1% PVP K-30 were exposed to forced degradation by basic hydrolysis where there was significant hydrolysis is present (FIG. 16, RT 11.410 and RT 13.529) and no oxidation related substances are seen. However, there is presence of a significant amount of LLD at RT 15.195.

Previous studies with forced basic hydrolysis and the presented HPLC chromatography analysis under similar conditions demonstrated 100% degradation of LLD. As demonstrated herein, inclusion of Kollidon K-30 (Povidone K-30) confers stability and resistance to degradation for solutions of LLD that has not been previously reported. Accordingly, the present disclosure includes solutions of stable LLD comprising Povidone K-30.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

In order that the invention described may be more fully understood, the following examples are set forth. The examples described in this application are offered to illustrate the methods and compositions provided herein and are not to be construed in any way as limiting their scope.

EXAMPLES

Example 1: Formulations of LLD were prepared according to Table 10. The formulations were prepared as a concentrated formulations comprising the addition of Kollidon K-12 (PVP) to NMP to dissolve the PVP then adding the LLD API to the NMP:PVP solution at the specific concentration. The resulting concentrate is a true solution of LLD in NMP:PVP. The diluents were prepared separately by dissolving sodium chloride in deionized water without a pH adjustment. The dilutions were performed by addition of concentrate to the diluent in a 1:4 ratio. The diluted formulations, as the final drug solution, were then subject to forced degradation study by exposure to fixed amounts of sodium hydroxide to perpetuate basic hydrolysis and fixed amounts of hydrogen peroxide to perpetuate oxidation. The resulting solutions were neutralized with acid to neutral pH or inactivated peroxide by enzymatic activity. The resulting solutions were analyzed by HPLC gradient method with DAD detection. A summary of results of these analyses are provided in Table 11 and demonstrate that certain formulations provided herein exhibit substantial protection of LLD degradation. Solutions of were analyzed over a 7 day period at T0 (within 4 hours of dilution), 2, 3, and 7 day held at ambient room temperatures. It is observed there is no oxidation degradation observed throughout the 7 day period for each of these solutions, thus the polar aprotic solvent in combination with PVP, a polar aprotic polymer, mitigate the oxidation of LLD in presence of saline. It is also observed that hydrolysis occurs as LLD Impurity 1 and LLD Impurity 2 for each of these formulations. There is a distinct trend of increasing degradation as the concentration of PVP is reduced from 4.0% to 0.4%. There is a distinct trend of increasing degradation as time passes from T0 to 7-day ambient RT for each of the formulations 1001 to 1004. However, there is a significant difference observed in concentrations of PVP greater than 2% to 4% compared to those observed at 0.4% to 0.8% PVP. At 7 days of solution stability the total RC, is 15-fold more degradation by hydrolysis occurring for the 0.4% PVP solution compared to the 4.0% PVP solution.

TABLE 10

| | 1001-1004 Formulas | | | |
|---|---|---|---|---|
| Exp # | Formulation LLD-PVP-NMP (mg/mL) | Diluent | Final Dilution [LLD]/[PVP]/[NMP] | Apparent pH |
| 1001 | 2.5/20/977.5 | 0.9% NaCl | 0.05%/0.4%/19.6% | ~5.2 |
| 1002 | 2.5/40/957.5 | 0.9% NaCl | 0.05%/0.8%/19.2% | ~5.0 |
| 1003 | 2.5/100/897.5 | 0.9% NaCl | 0.05%/2.0%/18.0% | ~5.2 |
| 1004 | 2.5/200/797.5 | 0.9% NaCl | 0.05%/4.0%/16.0% | ~4.8 |

TABLE 11

| 1001-1004 Results (% Peak Area Response) | | | | |
|---|---|---|---|---|
| Exp # | T0 | 2-day RT | 3-day RT | 7-day RT |
| 1001 | LLD-99.63 | LLD-97.00 | LLD-95.23 | LLD-90.53 |
| | Imp 1-0.27 | Imp 1-2.24 | Imp 1-3.57 | Imp 1-7.02 |
| | Imp 2-0.07 | Imp 2-0.71 | Imp 2-1.16 | Imp 2-2.41 |
| 1002 | LLD-99.76 | LLD-98.22 | LLD-96.92 | LLD-92.90 |
| | Imp 1-0.17 | Imp 1-1.30 | Imp 1-2.29 | Imp 1-5.25 |
| | Imp 2-0.03 | Imp 2-0.41 | Imp 2-0.75 | Imp 2-1.82 |
| 1003 | LLD-99.81 | LLD-99.59 | LLD-99.01 | LLD-96.74 |
| | Imp 1-0.05 | Imp 1-0.25 | Imp 1-0.61 | Imp 1-2.26 |
| | Imp 2-ND | Imp 2-0.07 | Imp 2-0.19 | Imp 2-0.78 |
| 1004 | LLD-99.55 | LLD-99.62 | LLD-99.57 | LLD-98.80 |
| | Imp 1-0.03 | Imp 1-0.07 | Imp 1-0.12 | Imp 1-0.42 |
| | Imp 2-ND | Imp 2-0.02 | Imp 2-0.04 | Imp 2-0.18 |

Example 2: Formulations of LLD were prepared according to Table 12 in the same manner as above in Example 1 with the exception of the addition of buffer constituents sodium bicarbonate and citric acid monohydrate for adjustment of pH. The formulations were then subjected to forced degradation and analyzed by HPLC in the same manner as above in Example 1. Results of this analysis are provided in Table 13 and demonstrate that certain formulations provided herein exhibit substantial protection of LLD degradation. Diluted solutions were analyzed over a 7 day period at T0 (within 4 hours of dilution), 2, 3, 4 and 7 day held at ambient room temperatures. There is no oxidation degradation observed throughout the 7 day period for each of these solutions, thus the polar aprotic solvent in combination with PVP, a polar aprotic polymer, mitigate the oxidation of LLD in presence of buffer system. It is observed hydrolysis occurs as LLD Impurity 1 and LLD Impurity 2 for each of these formulations. The formulations below evaluated addition of citric acid monohydrate to the entry solutions and sodium bicarbonate to the diluent solution. As these were fixed concentrations, no pH adjustment was performed, and the resulting pH is reported. There is a distinct difference in formulations 1001 to 1004 above compared to 10014 to 1004-IV with a significant decrease in hydrolysis observed in presence of NMP:PVP and a weak organic acid, such as citric acid monohydrate. The trend of increasing degradation as time passes from T0 to 7-day ambient RT for each of the formulations 1001-I to 1004-IV. However, there is a significant difference observed in 1003-III and 1004-IV due to a low apparent pH of ~4.5. Thus, solutions of LLD are shown to more stable with lower pH with Total RC~0.15% at 7 days ambient temperature compared to those of higher pH with ~5.0. However, a more appropriate physiological pH should be targeted between about pH 5.0 to about pH 7.0 is preferable. It should be noted that citric acid monohydrate alone is not sufficient to inhibit both hydrolysis and oxidation degradation events.

TABLE 12

1001-I-1002-II-1003-III-1004-IV

| Exp # | Formulation (mg/mL) LLD-PVP-NMP-Citric Acid | Diluent | Final Dilution [LLD]/[PVP]/[NMP]/[Citric Acid] | Apparent pH |
|---|---|---|---|---|
| 1001-I | 2.5/20/970.5/7 | 0.9% NaCl w/ Sodium Bicarbonate | 0.05%/0.4%/19.4%/0.14% | ~5.7 |
| 1002-II | 2.5/40/950.5/7 | 0.9% NaCl w/ Sodium Bicarbonate | 0.05%/0.8%/19.0%/0.14% | ~5.7 |
| 1003-III Low pH | 2.5/100/877.5/20 | 0.9% NaCl w/ Sodium Bicarbonate | 0.05%/2.0%/17.6%/0.4% | ~4.5 |
| 1004-IV Low pH | 2.5/200/777.5/20 | 0.9% NaCl w/ Sodium Bicarbonate | 0.05%/4.0%/15.6%/0.4% | ~4.5 |

TABLE 13

1001-I - 1002-II - 1003-III - 1004-IV Results (% Peak Area Response)

| Exp # | T0 | 2-day RT | 3-day RT | 4-day RT | 7-day RT |
|---|---|---|---|---|---|
| 1001-I | LLD - 99.98<br>Imp 1 - 0.11<br>Imp 2 - ND | LLD - 99.63<br>Imp 1 - 0.25<br>Imp 2 - 0.07 | LLD - 99.46<br>Imp 1 - 0.38<br>Imp 2 - 0.12 | LLD - 99.23<br>Imp 1 - 0.54<br>Imp 2 - 0.18 | LLD - 98.28<br>Imp 1 - 1.21<br>Imp 2 - 0.44 |
| 1002-II | LLD - 99.86<br>Imp 1 - 0.10<br>Imp 2 - ND | LLD - 99.65<br>Imp 1 - 0.23<br>Imp 2 - 0.06 | LLD - 99.48<br>Imp 1 - 0.34<br>Imp 2 - 0.11 | LLD - 99.29<br>Imp 1 - 0.49<br>Imp 2 - 0.16 | LLD - 98.48<br>Imp 1 - 1.07<br>Imp 2 - 0.40 |
| 1003-III Low pH | LLD - 99.87<br>Imp 1 - ND<br>Imp 2 - ND | LLD - 99.75<br>Imp 1 - 0.01<br>Imp 2 - ND | LLD - 99.80<br>Imp 1 - 0.03<br>Imp 2 - 0.03 | Not Tested | LLD - 99.54<br>Imp 1 - 0.06<br>Imp 2 - 0.09 |
| 1004-IV Low pH | LLD - 99.68<br>Imp 1 - ND<br>Imp 2 - ND | LLD - 99.64<br>Imp 1 - 0.06<br>Imp 2 - 0.02 | LLD - 99.59<br>Imp 1 - 0.02<br>Imp 2 - 0.03 | Not Tested | LLD - 99.16<br>Imp 1 - 0.05<br>Imp 2 - 0.09 |

Example 3: Formulations of LLD were prepared according to Table 14 in the same manner as Example 1 with the exception of addition of the higher concentration of citric acid monohydrate in the entry solution for the lower concentrations of PVP for comparison to Example 2 formulations 10014 and 1002-II and adjustment of the sodium bicarbonate concentration in diluent to achieve targeted pH~5.7. The formulations were then subjected to forced degradation and analyzed by HPLC in the same manner as Example 1. Results of this analysis are provided in Table 15 and demonstrate that certain formulations provided herein exhibit substantial protection of LLD degradation. Diluted solutions were analyzed over a 7-day period at T0 (within 4 hours of dilution), 2 and 7 day held at ambient room temperatures. There is no oxidation degradation observed throughout the 7-day period for each of these solutions, thus the polar aprotic solvent in combination with PVP, a polar aprotic polymer, mitigate the oxidation of LLD in presence of buffer system. It is observed hydrolysis occurs as LLD Impurity 1 and LLD Impurity 2 for each of these formulations. There is a distinct difference in formulations 1001-Ib to 1002-IIb compared to 1001-I and 1002-II with a significant decrease (~50% reduction) in hydrolysis observed in presence of NMP:PVP and a weak organic acid, such as citric acid monohydrate.

TABLE 14

1001-Ib - 1002-IIb

| Exp # | Formulation (mg/mL) LLD - PVP - NMP - Citric Acid | Diluent | Final Dilution [LLD]/[PVP]/[NMP]/[Citric Acid] | Apparent pH |
|---|---|---|---|---|
| 1001-Ib | 2.5/20/957.5/20 | 0.9% NaCl w/Sodium Bicarbonate | 0.05%/0.4%/19.2%/0.4% | ~5.7 |
| 1002-IIb | 2.5/40/937.5/20 | 0.9% NaCl w/Sodium Bicarbonate | 0.05%/0.8%/18.8%/0.4% | ~5.7 |

TABLE 15

1001-Ib - 1002-IIb Results (% Peak Area Response)

| Exp # | T0 | 2-day RT | 7-day RT |
|---|---|---|---|
| 1001-Ib | LLD - 99.87<br>Imp 1 - 0.06<br>Imp 2 - ND | LLD - 99.73<br>Imp 1 - 0.19<br>Imp 2 - 0.05 | LLD - 99.07<br>Imp 1 - 0.63<br>Imp 2 - 0.23 |
| 1002-IIb | LLD - 99.88<br>Imp 1 ~0.06<br>Imp 2 - ND | LLD - 99.73<br>Imp 1 - 0.18<br>Imp 2 - 0.05 | LLD - 99.10<br>Imp 1 - 0.61<br>Imp 2 - 0.23 |

Example 4: Formulations of LLD were prepared according to Table 16 in the same manner as above in Example 1 with the exception of the addition of buffer constituents sodium bicarbonate and citric acid monohydrate for adjustment of pH. The formulations were then subjected to forced degradation and analyzed by HPLC in the same manner as above in Example 1. Results of this analysis are provided in Table 17 and demonstrate that certain formulations provided herein exhibit substantial protection of LLD degradation. Diluted solutions were analyzed over a 7 day period at T0 (within 4 hours of dilution), 2, and 7 day held at ambient room temperatures. There is no oxidation degradation observed throughout the 7-day period for each of these solutions, thus the polar aprotic solvent in combination with PVP, a polar aprotic polymer, mitigate the oxidation of LLD in presence of buffer system. It is observed hydrolysis occurs as LLD Impurity 1 and LLD Impurity 2 for each of these formulations. The formulations below evaluated addition of citric acid monohydrate to the entry solutions and sodium bicarbonate to the diluent solution. As these were fixed concentrations, no pH adjustment was performed, and the resulting pH is reported. However, there is a difference observed in the remade formulations of 1003-III and 1004-IV with adjustment to sodium bicarbonate level from original pH of ~4.5 to pH~5.5. A slight increase in hydrolysis occurs as a result of the more physiologically acceptable pH.

TABLE 16

REMAKE 1003-III - 1004-IV

| Exp # | Formulation (mg/mL) LLD - PVP - NMP - Citric Acid | Diluent | Final Dilution [LLD]/[PVP]/ [NMP]/ [Citric Acid] | Apparent pH |
|---|---|---|---|---|
| 1003-III | 2.5/100/877.5/20 | 0.9% NaCl w/Sodium Bicarbonate | 0.05%/2.0%/17.6%/ 0.4% | ~5.5 |
| 1004-IV | 2.5/200/777.5/20 | 0.9% NaCl w/Sodium Bicarbonate | 0.05%/4.0%/15.6%/ 0.4% | ~5.5 |

TABLE 17

REMAKE 1003-III - 1004-IV Results (% Peak Area Response)

| Exp # | T0 | 1-day RT | 2-day RT | 7-day RT |
|---|---|---|---|---|
| 1003-III | LLD - 99.87 Imp 1 - ND Imp 2 - ND | LLD - 99.67 Imp 1 - 0.15 Imp 2 - 0.05 | LLD - 99.41 Imp 1 - 0.32 Imp 2 - 0.11 | LLD - 98.34 Imp 1 - 1.02 Imp 2 - 0.39 |
| 1004-IV | LLD - 99.68 Imp 1 - ND Imp 2 - ND | LLD - 99.50 Imp 1 - 0.15 Imp 2 - 0.05 | LLD - 99.27 Imp 1 - 0.31 Imp 2 - 0.11 | LLD - 98.04 Imp 1 - 0.98 Imp 2 - 0.38 |

Example 5: Consequences of order of addition of components on preparation of solutions, such as entry solutions, of the present technology were investigated. Entry solutions were prepared according to two different orders of ingredient addition as shown in Table 18.

TABLE 18

LLD-SC - Entry Solution (ES) Order of Addition

| Ingredients | ES (mg/mL (%)) | 1st Order of Addition | 2nd Order of Addition |
|---|---|---|---|
| Lenalidomide (LLD) | 13.0 (1.3%) | (1) | (3) After PVP is dissolved, add LLD, dissolve |
| Kollidon K-12 (PVP) | 100.0 (10.00%) | (3) Dissolve | (1) |
| n-methyl-2-pyrrolidone Pharmasolve (NMP) | 887.0 (88.7%) | (2) | (2) Dissolve PVP |

For the first order of addition, the ES was prepared by adding LLD, NMP and PVP in relatively the same time sequence where no complete dissolution of API or PVP was allowed prior to addition of additional components. Therefore, dissolution of LLD and PVP in presence of NMP occurs at approximately the same time. The ES was then diluted with diluent to a final concentration of ~0.5 mg/mL LLD. When ES was prepared in this manner, according to the first order of addition, a small amount of a white flaky unknown precipitate was observed floating freely in 20 mL volume of the final diluted formulation. The unknown precipitate was isolated and identified by FTIR to be a mixture/complex of LLD and PVP.

For the second order of addition, the ES was prepared by adding PVP then adding NMP, followed by dissolution. After PVP dissolution, LLD was added and dissolved. The ES was then diluted to a final concentration of ~0.5 mg/mL LLD. With preparation of the ES according to this second order of addition, no white precipitate was observed.

Without wishing to be bound by theory, it is thought that the precipitation phenomenon occurs when there are relatively high concentrations of LLD present in high concentrations of PVP. Accordingly, when both solids are dissolved at the same time, there is a higher potential for direct interactions. At lower drug concentrations of LLD, such as ES formulations made with 2.5 mg/mL LLD, the precipitation in dilute product was not observed. This is likely due to the significantly lower concentrations of LLD and resulting lower relative interaction incidence.

However, at higher drug concentrations of LLD, such as ES formulations made with 13 mg/mL LLD, the relative interaction of LLD and PVP is more prevalent. Therefore, a white precipitate was observed in diluted solutions when the first order of addition was followed for higher concentrations of LLD. Upon further examination of the ES, solutions prepared according to the first order of addition, were observed to contain clear gels. Again, without wishing to be bound by theory, it is hypothesized that the presence of these clear gels in the ES, and solid particulates in diluted solution, indicates the presence of a complex of LLD and PVP. These complexes are believed to form when LLD and PVP solid raw materials are presented into NMP. This results in formation of high concentration pockets of LLD in a dissolved state in proximity to high concentration pockets of PVP in a dissolved state, as dissolution continues until homogeneity is reached during mixing/agitation. These pockets of LLD and PVP allow for interaction and production of precipitate. Accordingly, these findings demonstrate the importance of carefully controlling the order of addition of components in production of solutions, such as ES, of the present technology.

Example 6: Evaluation of a Two-Part Lenalidomide System

Obtaining lenalidomide stability in an aqueous solution is challenging at physiological pH, and as such, it was determined to pursue development of a two (2) part system, similar to a lyophilization product and diluent. The intent of the formulation is to incorporate the API into a vehicle to obtain solubility and maintain stability with ease of processing through sterile filtration to obtain a fill/finish drug product. This active drug-containing formulation is referred to as the Entry Solution (ES) as it enters the drug into solution and is readily prepared for dilution. The diluent solution (DS) is the formulated diluent to ensure the final dilute drug product maintains solubility of the lenalidomide, maintains buffering capacity, and keeps the osmolality of the product within an acceptable range.

An evaluation of NMP and povidone at various concentrations in a simple buffer system (0.9% sodium chloride) was performed. The analytical results are presented in Table 3. the time in formulation, Kollidon 30 was utilized as the povidone component. The diluent system for this study was 0.9% saline for comparative purposes in early work. The formulation was tested initially for pH, then Assay and related substances at each time point. As shown here, 7 days of room temperature stability was obtained in the presence of NMP.

TABLE 19

Impact to Potency of LLD and Impurity Formulation from Incorporation of Povidone and N-Methyl-2-Pyrrolidone in Lenalidomide Formulation

| Sample | Formulation (wt. %) [LLD]/[PVP]/[NMP]/[NaCl] | pH | T0 | 2-day RT | 3-day RT | 7-day RT |
|---|---|---|---|---|---|---|
| 1001 | 0.05%/0.4%/19.6%/0.9% | 5.2 | 99.63% | 97.00% | 95.23% | 90.53% |
| | | | Imp 1 | Imp 1 | Imp 1 | Imp 1 |
| | | | 0.27% | 2.24% | 3.57% | 7.02% |
| | | | Imp 2 | Imp 2 | Imp 2 | Imp 2 |
| | | | 0.07% | 0.71% | 1.16% | 2.41% |
| 1002 | 0.05%/0.8%/19.6%/0.9% | 5.0 | 99.76% | 98.22% | 96.92% | 92.90% |
| | | | Imp 1 | Imp 1 | Imp 1 | Imp 1 |
| | | | 0.17% | 1.30% | 2.29% | 5.25% |
| | | | Imp 2 | Imp 2 | Imp 2 | Imp 2 |
| | | | 0.03% | 0.41% | 0.75% | 1.82% |
| 1003 | 0.05%/2.0%/19.6%/0.9% | 5.2 | 99.81% | 99.59% | 99.01% | 96.74% |
| | | | Imp 1 | Imp 1 | Imp 1 | Imp 1 |
| | | | 0.05% | 0.25% | 0.61% | 2.26% |
| | | | Imp 2 | Imp 2 | Imp 2 | Imp 2 |
| | | | ND | 0.07% | 0.19% | 0.78% |
| 1004 | 0.05%/4.0%/19.6%/0.9% | 4.8 | 99.55% | 99.62% | 99.57% | 98.80% |
| | | | Imp 1 | Imp 1 | Imp 1 | Imp 1 |
| | | | 0.03% | 0.07% | 0.12% | 0.42% |
| | | | Imp 2 | Imp 2 | Imp 2 | Imp 2 |
| | | | ND | 0.02% | 0.04% | 0.18% |

ND = Not Detected

Higher concentrations of Kollidon 12, a parenteral grade of povidone, were found to be equivalent to lower concentrations of Kollidon 25 and 30.

To adjust to a final formulation decision, osmolality and pH specifications were considered. The best stability was demonstrated in the range of pH 4.5 to 5.0. Osmolality was also adjusted by incorporating a dilution scheme to optimize drug concentration, NMP concentration and maintain osmolality of about 300-600 mOsm/kg. Final osmolality is about 450-500 mOsm/kg in the final composition as listed in Table 20, below.

The final formulation chosen comprises an Entry Solution and a Diluent Solution. The Entry Solution contains Lenalidomide and n-Methyl-2-Pyrrolidone. The Diluent Solution contains povidone as Kollidon 12, Citric Acid Monohydrate, and Sodium Bicarbonate in Water for Injection. The combination of povidone, citric acid monohydrate, sodium bicarbonate and the API contribute to the pH of the system of approximately pH 5.

TABLE 20

Final Composition of Entry Solution, Diluent Solution, and Final Dilution

| Volume for Dilution Schema | Entry Solution 1 mL | Diluent Solution 25 mL | Final Dilution Drug Product 26 mL |
|---|---|---|---|
| Lenalidomide (LLD) | 13 mg/mL (1.3 wt.%) | — | 0.5 mg/mL (0.05 wt.%) |
| Kollidon K-12 (PVP) | — | 75.0 mg/mL (7.5 wt.%) | 72.1 mg/mL (7.21 wt.%) |
| N-methyl-2-pyrrolidone Pharmasolve (NMP) | 987 mg/mL (98.7 wt.%) | — | 37.96 mg/mL (3.796 wt.%) |
| Sodium Bicarbonate (NaHCO$_3$) | — | 3.5 mg/mL (0.35 wt.%) | 3.4 mg/mL (0.34 wt.%) |
| Citric Acid Monohydrate | — | 4.7 mg/mL (0.47 wt.%) | 4.5 mg/mL (0.45 wt.%) |
| Water for Injection | — | 916.8 mg/mL (91.68 wt.%) | 881.5 mg/mL (88.15 wt.%) |
| Total Composition | 1000 mg/mL (100 wt.%) | 1000 mg/mL (100 wt.%) | 1000 mg/mL (100 wt.%) |

An embodiment of the formulation comprises two (2) separate vials prepared for the drug product to be combined later at time of administration to make up the final drug dilution. The first vial shall comprise an active pharmaceutical ingredient combined with a solvent, substantially free of water, as a separately prepared solution. Combinations of other excipients soluble in the same solvent, substantially free of water, may be incorporated, such as but not limited to, buffer excipients, polymer(s), solubilizing excipients, emulsifiers, crystallization inhibitors, and others. The second vial shall comprise the diluent solution, substantially free of the API, such that the diluent is a water-based solution comprising, buffers, polymers, solubilizing excipients, humectants, emulsifiers, crystallization inhibitors, osmolality modifiers, pH modifiers, stabilizers, antioxidants, protectants, or preservative agents.

TABLE 21

Embodiments of the active pharmaceutical ingredient solution may include but not limited to the following components.

| Ingredient | Final Dilution Concentration (wt. %) |
|---|---|
| Lenalidomide or other IMiD API | ~0.05% to about 30% |
| Pharmasolve (NMP) | ~60% to about 99.9% |
| Kollidon K-12 (PVP) | Absent (0%) to about 10% |

TABLE 22

Embodiments of the diluent solution may include but not limited to the following components.

| Ingredient | Final Dilution Concentration (wt. %) |
|---|---|
| Pharmasolve (NMP) | ~0.1% to about 30% |
| Kollidon K-12 (PVP) | ~0.1% to about 10% |
| Citric Acid | ~0.01% to about 2% |
| Sodium Bicarbonate | ~0.01% to about 2% |
| Water | qs (~56%-99.78%) |

Diluent is essentially free of the primary active ingredient, such as Lenalidomide or other IMiD.

TABLE 23

Embodiments of the final dilution may include but not limited to the following components.

| Ingredient | Final Dilution Concentration (wt. %) |
|---|---|
| Lenalidomide | ~0.05% to about 1% (0.5 mg/mL to about 10 mg/mL) |
| Pharmasolve (NMP) | ~0.1% to about 30% |
| Kollidon K-12 (PVP) | ~0.1% to about 10% |
| Citric Acid | ~0.01% to about 2% |
| Sodium Bicarbonate | ~0.01% to about 2% |
| Water | qs (~55%-99.73%) |

TABLE 24

A specific embodiment of the final dilution is listed below.

| Ingredient | Final Dilution Concentration (wt.%) |
|---|---|
| Lenalidomide | ~0.05% |
| Pharmasolve (NMP) | ~4% |
| Kollidon K-12 (PVP) | ~7% |
| Citric Acid | ~0.5% |
| Sodium Bicarbonate | ~0.3% |
| Water | qs (~88.15%) |

TABLE 25

Another specific embodiment of the final dilution composition is listed below.

| Ingredient | Final Dilution Concentration (wt.%) |
|---|---|
| Lenalidomide | ~0.1% |
| Pharmasolve (NMP) | ~7% |
| Kollidon K-12 (PVP) | ~7% |
| Citric Acid | ~0.5% |
| Sodium Bicarbonate | ~0.3% |
| Water | qs (~85.1%) |

TABLE 26

Another specific embodiment of the final dilution composition is listed below.

| Ingredient | Final Dilution Concentration (wt.%) |
|---|---|
| Lenalidomide | ~0.15% or 1.5 mg/mL |
| Pharmasolve (NMP) | ~9% |
| Kollidon K-12 (PVP) | ~7% |
| Citric Acid | ~0.5% |
| Sodium Bicarbonate | ~0.3% |
| Water | qs (~82.05%) |

TABLE 27

Another specific embodiment of the final dilution composition is listed below.

| Ingredient | Final Dilution Concentration (wt.%) |
|---|---|
| Lenalidomide | ~0.225% |
| Pharmasolve (NMP) | ~11% |
| Kollidon K-12 (PVP) | ~7% |
| Citric Acid | ~0.5% |
| Sodium Bicarbonate | ~0.3% |
| Water | qs (~80.975%) |

TABLE 28

Another specific embodiment of the final dilution composition is listed below.

| Ingredient | Final Dilution Concentration (wt.%) |
|---|---|
| Lenalidomide | ~0.3% |
| Pharmasolve (NMP) | ~15% |
| Kollidon K-12 (PVP) | ~7% |
| Citric Acid | ~0.5% |
| Sodium Bicarbonate | ~0.3% |
| Water | qs (~76.9%) |

It was also found that the formulation should not contain sodium metabisulfite as an antioxidant due to direct interaction with lenalidomide or APIs or excipients comprising a primary amine functional group.

It should be noted that the features illustrated in the drawings are not necessarily drawn to scale and features of one embodiment may be employed with other embodiments as the skilled artisan would recognize, even if not explicitly stated herein. Descriptions of well-known components and processing techniques may be omitted so as to not unnecessarily obscure the embodiments.

While multiple embodiments are disclosed, still other embodiments of the present invention will become apparent to those skilled in the art from this detailed description. The invention is capable of myriad modifications in various obvious aspects, all without departing from the spirit and scope of the present invention. Accordingly, the drawings and descriptions are to be regarded as illustrative in nature rather than restrictive.

What is claimed is:

1. A stable liquid formulation of lenalidomide for parenteral administration, comprising lenalidomide, n-methyl-2-pyrrolidone, polyvinylpyrrolidone K12, a buffering agent comprising citric acid and sodium bicarbonate, and water, wherein the lenalidomide is present in solubilized form at a concentration ranging from about 0.01 wt. % to about 0.8 wt. % based on the total weight of the liquid formulation, the n-methyl-2-pyrrolidone is present at a concentration ranging from about 1 wt. % to about 20 wt. % based on the total weight of the liquid formulation, the polyvinylpyrrolidone K12 is present at a concentration ranging from about 1 wt. % to about 10 wt. % based on the total weight of the liquid formulation, the citric acid is present at a concentration ranging from about 0.01 wt. % to about 2 wt. % based on the total weight of the liquid formulation, the sodium bicarbonate is present at a concentration ranging from about 0.01 wt. % to about 2 wt. % based on the total weight of the liquid formulation, and the water is at a concentration ranging from about 55 wt. % to about 99.8 wt. % based on the total weight of the liquid formulation, wherein the liquid formulation has an osmolality ranging from about 300 mOsm/kg to about 600 mOsm/kg when the lenalidomide is present at a concentration of about 0.05 wt. % based on the total weight of the liquid formulation, and the liquid formulation has a pH between about 4.5 and about 5.5.

2. The stable liquid formulation of claim 1, wherein the stable liquid formulation is prepared by combining an entry solution and a diluent solution, wherein the ratio of the entry solution to the diluent solution is from about 1:1 to about 1:50, wherein the entry solution and the diluent solution are maintained separately prior to administration to a patient, at which time the entry solution and diluent solution are combined to form a final solution for administration to the patient.

3. The stable liquid formulation of claim 2, wherein the lenalidomide is present in the entry solution at a concentration ranging from about 0.05 wt. % to about 5 wt. %, and wherein the vent n-methyl-2-pyrrolidone is present in the entry solution at a concentration ranging from about 95 wt. % to about 99 wt. %, based on the total weight of the entry solution.

4. The stable liquid formulation of claim 2, wherein the polyvinylpyrrolidone K12 is present in the diluent solution at a concentration ranging from about 0.1 wt. % to about 10 wt. %, wherein the water is present in the diluent solution at a concentration ranging from about 56 wt. % to about 99.8 wt. %, and wherein the n-methyl-2-pyrrolidone is present in the diluent solution at a concentration of up to about 10 wt. %, based on the total weight of the diluent solution.

5. The stable liquid formulation of claim 2, wherein the citric acid is present in the diluent solution at a concentration ranging from about 0.01 wt. % to about 5 wt. % and the sodium bicarbonate is present in the diluent solution at a concentration ranging from about 0.01 wt. % to about 5 wt. %, based on the total weight of the diluent solution.

6. The stable liquid formulation of claim 1, wherein the parenteral administration is intravenous, subcutaneous, or infusion.

* * * * *